(12) United States Patent
Mereu et al.

(10) Patent No.: US 7,507,721 B2
(45) Date of Patent: Mar. 24, 2009

(54) MACROLIDES WITH ANTIINFLAMMATORY ACTIVITY

(75) Inventors: Andrea Mereu, Grandate (IT); Mauro Napoletano, Milan (IT); Fernando Ornaghi, Carlazzo (IT); Ermanno Moriggi, Busto Arsizio (IT); Franco Pellacini, Milan (IT)

(73) Assignee: Zambon Group S.p.A., Vicenza (IT)

( * ) Notice: Subject to any disclaimer, the term of this patent is extended or adjusted under 35 U.S.C. 154(b) by 366 days.

(21) Appl. No.: 10/587,623

(22) PCT Filed: Jan. 25, 2005

(86) PCT No.: PCT/EP2005/050312

§ 371 (c)(1),
(2), (4) Date: Jul. 26, 2006

(87) PCT Pub. No.: WO2005/075494

PCT Pub. Date: Aug. 18, 2005

(65) Prior Publication Data

US 2007/0167381 A1 Jul. 19, 2007

(30) Foreign Application Priority Data

Jan. 29, 2004 (IT) .......................... MI2004A0124

(51) Int. Cl.
*A61K 31/70* (2006.01)
*C07H 17/08* (2006.01)

(52) U.S. Cl. .................... 514/29; 536/7.2; 536/7.3; 536/7.4

(58) Field of Classification Search .............. 536/7.2, 536/7.3, 7.4
See application file for complete search history.

(56) References Cited

U.S. PATENT DOCUMENTS 5,215,980 A 6/1993 Jones

FOREIGN PATENT DOCUMENTS

| WO | WO 00/42055 | 7/2000 |
|---|---|---|
| WO | WO 2004/013153 | 2/2004 |

*Primary Examiner*—Elli Peselev
(74) *Attorney, Agent, or Firm*—Lucas & Mercanti, LLP

(57) ABSTRACT

Macrolide compounds of formula (I) wherein X, R, $R_1$, $R_2$, $R_3$ and $R_4$, have the meanings as defined in the specification, pharmaceutically acceptable salts thereof, pharmaceutical compositions containing them as active ingredient and the use thereof in the treatment and prophylaxis of inflammatory diseases, are described.

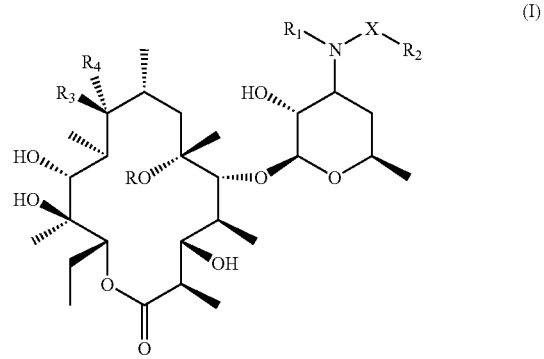

18 Claims, No Drawings

MACROLIDES WITH ANTIINFLAMMATORY ACTIVITY

This patent application claims the benefit of priority from Italian Patent Application No. MI 2004 A 000124 filed Jan. 29, 2004 through PCT application Ser. No. PCT/EP2005/050312 filed Jan. 25, 2005, the contents of which are incorporated herein by reference.

The present invention relates to macrolides endowed with antiinflammatory activity and, more particularly, it relates to 3'-amidic macrolide derivatives lacking cladinose with antiinflammatory activity, to pharmaceutically acceptable salts thereof and to pharmaceutical compositions containing them as active ingredient.

It is known that several antibiotics, in particular the class of 14-atom macrolide derivatives of erythromycin, are endowed with antiinflammatory proprierties in addition to their antibacterical activity [Clin. Immunother., (1996), 6, 454-464]. Erythromycin is a natural macrolide (The Merck Index, XIII edition, n° 3714, pag. 654) which had a very wide clinical use in treating the infections caused by Gram-positive bacteria, by some Gram-negative bacteria or by Mycoplasms.

The interest of the scientific community has recently turned to the immunomodulatory and antiinflammatory activities of erythromycin and derivatives thereof [Journal of Antimicrobial Chemotherapy, (1998), 41, Suppl. B, 37-46].

Macrolides have revealed effective in the treatment of inflammatory pathologies such as panbronchiolites [Thorax, (1997), 52, 915-918], bronchial asthma [Chest, (1991), 99, 670-673] and cystic fibrosis [The Lancet, (1998), 351, 420].

The in vitro activity of macrolides has revealed particularly effective in the modulation of the metabolic functions of some cells of the immune system such as neutrophils [The Journal of Immunology, (1997), 159, 3395-4005] and lymphocytes T [Life Sciences, (1992), 51, PL 231-236] and in the modulation of inflammation mediators such as interleukin 8 (IL8) [Am. J. Respir. Crit. Care Med., (1997), 156, 266-271] or interleukin 5 (IL-5) [patent applications EP 0775489 and EP 0771564, in the name of Taisho Pharmaceutical Co., Ltd].

The neutrophils, in particular, constitute the first cell line recruited in the site of infection or tissue lesion at a very early stage of an inflammatory response.

A not physiologic collection of neutrophils in the inflammed tissue, the activation thereof, the subsequent release of protease and the increase in the production of oxygen-reactive metabolites characterize some forms of inflammatory response which, in most cases, degenerate into pathologic conditions.

Thus, although the neutrophils are essential in the immune defence and in the inflammatory process, it is known that they are involved in pathologies deriving from the greatest part of chronic inflammatory conditions and from lesions from ischemic reperfusion (Inflammation and fever; Viera 'Stvrtinová, Jan Jakubovsky e Ivan Húlin; Academic Electronic Press, 1995).

In the same text the pathologies are reported therefor the influence of an altered functionality of the neutrophils in the genesis and/or development thereof is proved: thereamong there are cited atherosclerosis, damages by ischemic reperfusion, rheumatoid arthritis, psoriasis, vasculites and glomerulonephrites with autoimmune derivation, Crohn's disease and chronic pulmonary inflammations such as ARDS (adult respiratory distress syndrome).

COPD (chronic obstructive pulmonary disease) is a chronic pathology characterized by inflammation and progressive destruction of pulmonary tissue caused by massive presence of activated neutrophils with consequent release of metal proteinases and increase in the production of oxygen radicals [Am. J. Respir. Crit Care Med., 1996, 153, 530-534] [Chest, 2000, 117 (2 Suppl), 10S-14S].

The administration of macrolides to asthmatic subjects is accompanied by a reduction in the hypersecretion and bronchial hypersensibility consequent to an anti-oxydative and anti-inflammatory interaction with the phagocytes and in particular with the neutrophils; this interaction would prevent that several bioactive lipids, involved in the pathogenesis of bronchial asthma, from exerting their membrane-destabilizing proinflammatory activity (Inflammation, Vol. 20, No. 6, 1996).

The treatment with erythromycin, at low doses for long periods, is described to be effective in reducing the bronchial hypersensibility in the patients affected by asthma (Miyatake H. et al Chest, 1991, 99, 670-673, already cited).

In an additional study it was demonstrated that the same treatment, in patient affected by COPD, can significantly reduce the frequence and the risk of exacerbation caused by acute respiratory infections (CHEST 2001, 120, 730-733).

The obtained results cannot be ascribed to the antibiotic activity of the macrolide, but to the inhibition of the expression and of the release of the inflammatory cytokines.

According to the article mentioned above, the treatment should be preferably restricted to patients with high risk of COPD exacerbation due to the potential risk in creating resistant pathogenic strains.

The peculiar therapeutic effectiveness of macrolides in the pathologies wherein traditional antlinflammatory drugs, such as for example corticosteroides, have revealed uneffective [Thorax, (1997), 52, 915-918, already mentioned] justifies the great interest in this new potential class of antiinflammatories.

Nevertheless, the fact that classic macrolides have a powerful antibacterial activity does not allow an extended use of said macrolides in chronic treatment of inflammatory processes not caused by pathogenic microorganisms; in fact, this could cause the rapid creation of resistant strains.

Therefore, it would be desirable to dispose of new substances with macrolide structure having antiinflammatory activity and at the same time that are free of antibiotic properties.

For clarity sake, the formula of erythromycin wherein the numeration adopted in the present patent application is shown, is reported herebelow

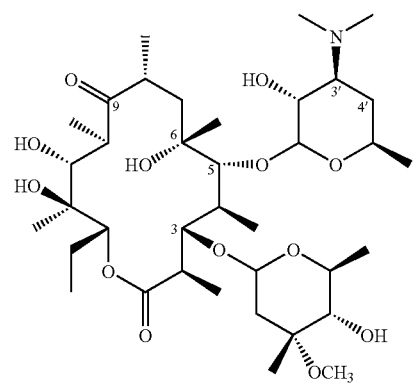

In literature some classes of erythromycin derivatives endowed with antibacterial activity are described.

In the patent application WO 99/16779 in the name of Abbott Laboratories ketolides, erythromycin derivatives, modified at 3' position and 6-O-substituted used in the treatment of bacterial infections, are described.

In the patent application JP 2001181294 (Hokuriku Pharmaceutical Co.) 9-oxyimino erythromycin derivatives esterificated at 3 and 3' position modified useful as antibacterial and antiulcer agents are described.

In the U.S. Pat. No. 3,928,387 (Hoffmann-La Roche Inc.) 3'-desdimethylamino-3',4'-dehydroerythromycin A 9-oxime and the erythronolide A 9-oxime as intermediates useful in the preparation of the antibiotic 1745A/X are described.

In the patent application EP 0254534 (Robinson, William S.) a very wide class of macrolides comprising erytronolide A 9-O-methyloxime and 9-oximino erythromycin A derivatives for example 3'-desdimethylamino-3',4'-dehydroerythromycin A 9-O-methyloxime, are described.

The patent application mentioned above claims compounds with antiviral activity. Furthermore, in literature some classes of etythromycin derivatives endowed with antiinflammatory activities are described.

For example, erythromycin derivatives modified at 3, 9, 11, and 12 position are claimed as powerful inhibitors of the IL-5 synthesis in the already mentioned Taisho European patent applications.

The use of crythromycin as antiinflammatory acting by reducing the release of interleukin 1 through the inhibition of the mammalian mdr-P glycoprotein is claimed in the patent application WO 92/16226 in the name of Smith-Kline Beecham Corporation.

In the patent application WO 00/42055 in the name of Zambon Group 3'-desdimethylamino-9-oxyimino macrolides endowed with antiinflammatory activity and deprived of antibiotic activity are described.

As told before, an effective contribution to the antiinflammatory activity exibited by macrolide compounds can be ascribed to the modifications induced on some metabolic functions of neutrophils.

The presence of L-cladinose at 3 position onto the ring of macrolide derivatives exerts a key structural role in modulating the above-mentioned metabolic-functional activities of neutrophils [The Journal of Immunology, 1997, 159, 3395-4005, already mentioned].

Accordingly, the sugar activity could be linked either to the importance of the same for cellular uptake of macrolide compounds and to its interaction with a cellular target involved in both the metabolic activities of the neutrophils.

The same neutral L-cladinose sugar was described as endowed with high antiinflammatory activity.

Pharmaceutical compositions containing cladinose or L-cladinose as an active agent for treating inflammatory conditions are disclosed in the International patent application No. WO 97/00684 in the name of Roussel Uclaf.

Now, we have surprisingly found that new 3'-amidic macrolide derivatives lacking the cladinose moiety are endowed with antiinflammatory activity and substantially free of antibiotic properties.

Therefore, object of the present invention is a compound of formula

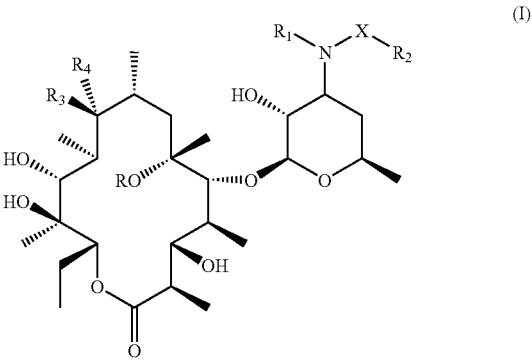

(I)

wherein

X is a —C(=O)—, —C(=O)—O—, —C(=O)—N—, —SO$_2$— or —SO$_2$—N— group;

R is a hydrogen atom or methyl;

$R_1$ is a hydrogen atom or a ($C_1$-$C_3$)alkyl group;

$R_2$ is a hydrogen atom, a (C1-C4)-alkoxy-(C1-C4)-alkyl group, a (C5-C7)-cycloalkyl group, a phenyl or a five- or six-membered heteroaryl having from one to three heteroatoms selected among nitrogen, oxygen and sulphur, a phenyl-($C_1$-$C_4$)-alkyl or heteroaryl-($C_1$-$C_4$)-alkyl group optionally substituted by 1 to 3 substituents selected among a ($C_1$-$C_4$)-alkyl group, a ($C_1$-$C_4$)-alkoxy group and halogen, or a chain of formula

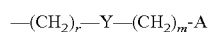

wherein

A is a phenyl or a five- or six-membered heteroaryl having from one to three heteroatoms selected among nitrogen, oxygen and sulphur, both ones optionally substituted by 1 to 3 substituents selected among a ($C_1$-$C_4$)-alkyl group, a ($C_1$-$C_4$)-alkoxy group and halogen;

Y represents O, S or $NR_6$ wherein $R_6$ is a hydrogen atom, a linear or branched ($C_1$-$C_3$) alkyl, a ($C_1$-$C_3$)-alkoxycarbonyl group or a benzyloxycarbonyl group;

r is an integer comprised between 1 and 3;

m is an integer comprised between 0 and 3;

$R_3$ is a hydroxy group or $R_3$ taken together with $R_4$ forms a (=O) group or a =N—O—$R_5$ group wherein $R_5$ is a hydrogen atom, a ($C_1$-$C_4$)-alkyl group, a benzyl or a —X—$R_2$ group wherein X and $R_2$ have the corresponding meanings mentioned above;

$R_4$ is a hydrogen atom or $R_4$ taken together with $R_3$ forms a (=O) group or a =N—O—$R_5$ group wherein $R_5$ has the meanings mentioned above;

and furthermore $R_2$ is a ($C_1$-$C_{10}$)-alkyl group or a ($C_4$-$C_{10}$)-alkyl group when, at the same time, X is a —C(=O)— group, $R_1$ is a ($C_1$-$C_3$)-alkyl group and $R_3$ is a hydroxy group or $R_3$ taken together with $R_4$ forms a =N—O—$R_5$ group wherein $R_5$ is different from —X—$R_2$;

and pharmaceutically acceptable salts thereof.

The compounds wherein $R_2$ is a ($C_1$-$C_3$)-alkyl group when, at the same time, X is a —C(=O)— group, $R_1$ is a ($C_1$-$C_3$)-alkyl group and $R_3$ is a hydroxy group or $R_3$ taken together with $R_4$ forms a =N—O—$R_5$ group wherein $R_5$ is different from —X—$R_2$ are described in the co-pending Italian patent application No. MI2002A001726 in the name of the same Applicant filed on 1 Aug. 2002.

The oximes of formula I can have Z or E configuration.

The compounds of formula I are antiinflammatory macrolides without antibiotic activity and therefore they are useful in the treatment and prophylaxis of inflammatory pathologies.

Specific examples of $(C_1-C_{10})$-alkyl groups are methyl, ethyl, n-propyl, i-propyl, n-butyl, s-butyl, t-butyl, n-pentyl, 1-methyl-butyl, 2-ethyl-propyl, 3-methyl-butyl, 3-methyl-2-butyl, n-esyl, eptyl, optyl, nonyl, decyl and the like.

As $(C_5-C_7)$-cycloalkyl group cyclopentyl, cycloesyl and cycloeptyl are meant.

Under halogen term a fluorine, chlorine, bromine and iodine atom are meant.

Under a 5- or 6-membered heteroaryl term having from 1 to 3 heteroatoms selected among nitrogen, oxygen and sulphur, heterocycles such as pyrrole, thiophene, furan, imidazole, pyrazole, thiazole, isothiazole, isoxazole, oxazole, pyridine, pyrazine, pyrimidine, pyridazine, triazole and thiadiazole are meant.

It is clear to the person skilled in the art that the substitution of the heteroaryls by partially or totally saturated forms as well as the presence of other substituents on the aromatic rings (phenyl or heteroaryls) provided in the $R_2$ meanings give origin to compounds which do not depart from the spirit and the scope of the present invention.

Preferred compounds of formula I are the ones wherein R, $R_1$, $R_2$ have the meanings defined in formula I, X is a —C(=O)—, —C(=O)—N— or —SO$_2$— group and $R_3$ is a hydroxy group or $R_3$ taken together with $R_4$ forms a (=O) group or a =N—O—$R_5$ group wherein $R_5$ is a hydrogen atom, methyl, benzyl or a —X—$R_2$ group wherein X and $R_2$ have the meanings as defined in the above formula I.

More preferred compounds within this group are the ones wherein $R_1$ is a hydrogen atom or methyl and $R_5$ is a hydrogen atom or a —X—$R_2$ group wherein X and $R_2$ have the meanings as defined in the above formula I.

Furthermore, still more preferred compounds belonging to this group are the ones wherein $R_2$ is a hydrogen atom, a $(C_1-C_4)$-alkoxy-$(C_1-C_4)$-alkyl group, a $(C_5-C_7)$-cycloalkyl group, a phenyl or a five or-six-membered heteroaryl having from one to three heteroatoms selected among nitrogen, oxygen and sulphur, a phenyl-$(C_1-C_4)$-alkyl or heteroaryl-$(C_1-C_4)$-alkyl group optionally substituted by 1 to 3 substituents selected among a $(C_1-C_4)$-alkyl group, a $(C_1-C_4)$-alkoxy group and halogen, or a chain of formula

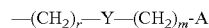

wherein

A is a phenyl or a heteroaryl selected among furan, thiophene, oxazole, imidazole, pyridine, pyrimidine and triazole both ones optionally substituted by 1 to 3 substituents selected among a $(C_1-C_4)$-alkyl group, a $(C_1-C_4)$-alkoxy group or halogen;

Y represents O, S or $NR_6$ wherein $R_6$ is a hydrogen atom or methyl;

r is an integer comprised between 1 and 3;

m is an integer comprised between 0 and 3;

and furthermore $R_2$ is a $(C_1-C_{10})$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

More preferred compounds within this group are the ones wherein $R_1$ is methyl and $R_2$ is a metoxy-$(C_1-C_3)$-alkyl group, a $(C_5-C_7)$-cycloalkyl group, a phenyl or a heteroaryl selected among furan, thiophene, oxazole and pyridine, a benzyl or heteroaryl-$(C_1-C_4)$-alkyl group optionally substituted by a substituent selected among a $(C_1-C_4)$-alkyl group, a metoxy group and halogen, or a chain of formula

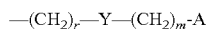

wherein

A is a phenyl or a heteroaryl selected among furan, thiophene, oxazole and pyridine, both ones optionally substituted by a substituent selected among a $(C_1-C_4)$-alkyl group, a metoxy group or halogen;

Y represents O, S or $NR_6$ wherein $R_6$ is a hydrogen atom;

r is an integer comprised between 1 and 3;

m is an integer selected between 0 and 1;

and furthermore $R_2$ is a $(C_1-C_7)$-alkyl group or a $(C_4-C_{10})$-alkyl group when, at the same time, X is a —(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

An additional class of preferred compounds is the class wherein R, $R_1$, $R_2$ and X have the meanings as defined in formula I, $R_3$ is a hydroxy group and $R_4$ is a hydrogen atom.

Still more preferred compounds belonging to this group are the ones wherein $R_1$ is a hydrogen atom or methyl and X is a —C(=O)—, —C(=O)—N— or —SO$_2$— group.

Still more preferred compounds belonging to this group are the ones wherein $R_2$ is a hydrogen atom a $(C_1-C_4)$-alkoxy-$(C_1-C_3)$-alkyl group, a $(C_5-C_7)$-cycloalkyl group, a phenyl or a five- or six-membered heteroaryl having from one to three heteroatoms selected among nitrogen, oxygen and sulphur, a phenyl-$(C_1-C_4)$-alkyl or heteroaryl-$(C_1-C_4)$-alkyl group optionally substituted by a substituent selected among a $(C_1-C_4)$-alkyl group, a $(C_1-C_4)$-alkoxy group and halogen, or a chain of formula

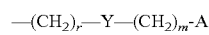

wherein

A is a phenyl or a heteroaryl selected among furan, thiophene, oxazole, imidazole, pyridine, pyrimidine and triazole both ones optionally substituted by a substituent selected among a $(C_1-C_4)$-alkyl group, a $(C_1-C_4)$-alkoxy group or halogen;

Y represents O, S or $NR_6$ wherein $R_6$ is a hydrogen atom or methyl;

r is an integer comprised between 1 and 3;

m is an integer selected among 0 and 3;

and furthermore $R_2$ is a $(C_1-C_7)$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

Still more preferred compounds belonging to this group are the ones wherein $R_1$ is methyl and $R_2$ is a hydrogen atom, a methoxy-$(C_1-C_3)$-alkyl group, a $(C_5-C_7)$-cycloalkyl group, a phenyl or a heteroaryl selected among furan, thiophene, oxazole and pyridine, a benzyl or heteroaryl-methyl group wherein heteroaryl is selected among furan, thiophene, oxazole and pyridine, optionally substituted by a substituent selected among a $(C_1-C_4)$-alkyl group, a metoxy group and halogen, or a chain of formula

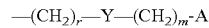

wherein

A is a phenyl or a heteroaryl selected among furan, thiophene, oxazole and pyridine, both ones optionally substituted by a substituent selected among a methyl group, a metoxy group or halogen;

Y represents O, S or $NR_6$ wherein $R_6$ is a hydrogen atom;

r is an integer comprised between 1 and 3;

m is an integer selected among 0 and 1;

and furthermore $R_2$ is a $(C_1-C_7)$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

Still more preferred compounds belonging to this group are the ones wherein $R_2$ is a methoxy-methyl group, a cycloesyl, a phenyl or a heteroaryl selected among furan, thiophene, oxazole and pyridine, a benzyl or thiophen-il-methyl group optionally substituted by a substituent selected among a methyl group, a metoxy group and halogen, or a chain of formula

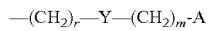
—(CH$_2$)$_r$—Y—(CH$_2$)$_m$-A wherein

A is a phenyl or pyridine, both ones optionally substituted by a metoxy group;

Y represents O, S or $NR_6$ wherein $R_6$ is a hydrogen atom;

r is an integer comprised between 1 and 3;

m is an integer selected between 0 and 1;

and furthermore $R_2$ is a $(C_1-C_7)$alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

An additional class of preferred compounds are the ones wherein the —X—$R_2$ substituent in the meanings of $R_5$ has the same meanings of the X and $R_2$ substituents at 3' position.

A further object of the present invention are the compounds of formula I having Z or E configuration on the oxime at 9 position, preferably E configuration.

Examples of pharmaceutically acceptable salts of the compounds of formula I are salts with organic and inorganic acids such as hydrochloric, hydrobromic, hydroiodic, nitric, sulfuric, phosphoric, acetic, tartaric, citric, benzoic, succinic and glutaric acid.

Specific examples of compounds according to the present invention, are the compounds of formula I wherein R and $R_4$ have the meanings as defined in formula I; X is —C(=O)—, —C(=O)—N— or —SO$_2$— group; $R_1$ is methyl; $R_2$ is hydrogen, methoxy-methyl, cycloesyl, phenyl, benzyl, 4-methylphenyl, 4-methoxy-phenyl, 4-fluorine-phenyl, 2-furyl, 3-pyridyl, 2-tiophenyl, 2-chlorine-3-pyridyl, 2-thiophen-yl-methyl, 3-methyl-5-oxazolyl, (4-methoxy-piridin-2-yl-methyl)-oxymethyl, phenyl-thio-methyl, methyl ethyl, t-butyl and eptyl; $R_3$ is hydroxy or $R_3$ taken together with $R_4$ forms a (=O) group or a =N—O—$R_5$ group wherein $R_5$ is hydrogen, acetyl, pivaloyl 4-methoxy-benzoyl, 2-thiophencarboxyl, 2-thiophen-acetyl.

The compounds of formula I, object of the present invention, are prepared by following a synthetic scheme which comprises the demethylation of the dimethylamino group at 3' position and the removal of the L-cladinose from the compounds of formula

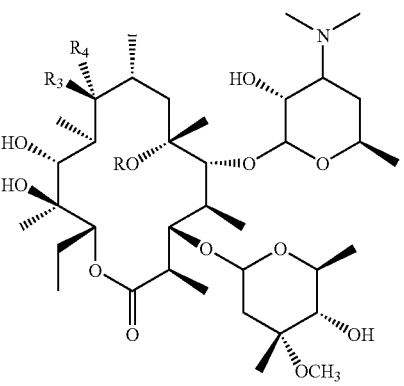

wherein R, $R_3$ and $R_4$ have the meanings as defined for the compounds of formula I and the following amidation of the primary or secondary aminic group at 3' position to give the compounds of formula I.

The compounds of formula II are erythromycin A or 6-O-methyl-erythromycin A (non-proprietary name: Clarithromicyn) or they are obtained therefrom by possible intervention at level of the ketonic group at 9 position onto the macrolide ring.

The ketonic group at 9 position can be reduced to give a hydroxy derivative or it can be treated with reagents suitable to obtain some oxymine derivatives.

The oximes of erythromycin A, with Z or E configuration, are known commercially available compounds and they can be prepared with conventional techniques such as, for example, the techniques mentioned in the U.S. Pat. No. 3,478,014 in the name of Pliva or the ones described in literature (J. C. Gasc et al: The Journal of Antibiotics; 44, 313-330, 1991).

The oximine derivatives of formula I wherein $R_5$ is different from a hydrogen atom can be prepared by direct synthesis or by the oxime functionalization through conventional techniques.

The macrolide derivatives showing at 9 position a hydroxy group are known compounds which can be obtained with conventional techniques, for example, by means of the treatment with reducing agents such as, for examples, the hydrides (sodium borohydride, lithium borohydride, sodium cyano borohydride, lithium aluminiumhydride) (Faghin, Journal of Antibiotics, 1990, 1334-1336) or by using catalytic hydrogenation.

Starting from such substrates, the preparation of the compounds of formula I comprises the demetylation of the dimethylamino group at 3' position carried out with conventional techniques such as, for example, the treatment with sodium acetate and iodine in the presence of an organic solvent as described in the U.S. Pat. No. 3,725,385 in the name of Abbott Laboratories, or the reaction with dialkyl-azadicarboxylate in acetone as described in the U.S. Pat. No. 6,433,151 in the name of Aventis Pharma.

To the obtained 3'-demethylated macrolide derivatives, the cladinose is removed by a hydrolysis carried out according to known techniques.

Preferably, cladinose removal is carried out by an acid catalyzed hydrolysis in the presence of a mineral acid such as, for example, sulfuric acid or hydrochloric acid and of a protic organic solvent such as, for example, water, methanol or ethanol.

The functionalization of the primary or secondary aminic group at 3' position, aimed at introducing —X— and $R_2$ substituents defined in formula I, is carried out by using amidation techniques known to the person skilled in the art.

In particular, such synthetic techniques relate to the common preparations of amides, sulfonamides, ureas, sulfonylureas and urethans starting from an aminic substrate. Preferably the X and $R_2$ substituents are introduced at the same time onto the molecule.

For example, the preparation of the amidic or sulfonamidic derivatives is usually carried out by treating the compounds 3' demethylated with suitable acyl chlorides or sulfonyl chlorides according to conventional techniques such as, for example, the reaction of the above-mentioned compounds in the presence of a base such as, for example, triethylamine and an organic solvent such as, for example, dichloromethane or tetrahydrofuran.

Furthermore, the preparation of the ureic derivatives is preferably carried out by using suitable isocyanates in the presence of an organic solvent such as, for example, dichloromethane.

Alternatively, the preparation of the derivatives bearing more complex amidic chains are synthetized by step processes.

For example, 3' demethylated derivatives are treated with an omega-chloroalcanoic (acetic, propionic or butirric) acid and N-cycloesylcarbodiimide in the presence of an organic solvent such as, for example, tetrahydrofuran, and the obtained derivative is used as substrate for introducing the ending part of the amidic chain in particular of the compounds of formula I wherein X is a —C(=O)— group and $R_2$ is a chain of formula —$(CH_2)_r$—Y—$(CH_2)$m-A.

In order to avoid interferences with functional groups possibly present in the positions wherein structural modifications are performed, a the person skilled in the art will carry out the reaction steps in a convenient and appropriate order.

Therefore, for example, the possible functionalization of the oxymino derivatives can take place just after the synthesis thereof, it can be carried out at the same time of the functionalization at 3' position or it can constitute the final step of the synthesis.

With reference to cladinose removal, this reaction can be carried out after the modifications to the ketonic group at 9 position, it can follow or precede the possible functionalization of the oxymino derivatives in the same position, it can follow or precede the possible intervention onto the dimethylamino group.

Preferably, the sugar hydrolysis is carried out after demethylation of the dimethylamino group at 3' position; however, in principle there are no interactions preventing the cladinose removal in another intermediate step or at the end of the synthetic process.

As mentioned above, the compounds of formula I object of the present invention are endowed with antiinflammatory activity and they have no antibiotic activity.

The pharmacological activity of the compounds of formula I has been evaluated in models of cutaneous inflammation compared to known macrolides, such as erythromycin and azithromycin, endowed with both antiinflammatory and antibiotic activity.

The antiinflammatory activity has been evaluated as inhibition of PMA-induced oedema in mouse ear (Phorbol Myristate Acetate).

The obtained results demonstrated that not only the compounds object of the present invention are very active as antiinflammatory agents but also that their and the antiinflammatory activity is higher than the activity of the comparison compounds.

The antibiotic activity has been evaluated "in vitro" as capability of inhibiting the growth of bacterial strains sensible to erythromycin.

The compounds of the present invention do not show antibiotic activity and therefore they can be used in chronic treatments of inflammatory processes without creating undesired resistence phenomena.

Therefore, it is clear to the person skilled in the art that the compounds of formula I, endowed with antiinflammatory activity and without antibiotic activity, can be useful in both the acute and chronic treatment and in the prophylaxis of inflammatory pathologies, in particular pathologies connected to altered cellular functionality of the neutrophils such as, for example, rheumatoid arthritis, vasculites, glomerular nephrites, psoriasis, atopic dermatitis, ulcerative colitis, Crohn's disease, damages by ischemic reperfusion, septic shock, atherosclerosis, ARDS, COPD and asthma.

The therapeutically effective amounts will depend upon age and upon the general physiological conditions of the patient, upon the administration route and upon the used pharmaceutical composition; the therapeutical doses will be generally comprised from about 10 and 2000 mg/day and preferably from about 30 and 1500 mg/day.

The compounds of the present invention for the use in the therapy and/or in the prophylaxis of the pathologies mentioned above will be preferably used in a pharmaceutical form suitable for oral, rectal, sublingual, parental, topic, transdermic and inhalatory administration.

Therefore, a further object of the present invention are pharmaceutical compositions comprising a therapeutically effective amount of a compound of formula I or a salt thereof in admixture with a pharmaceutically acceptable carrier.

The pharmaceutical compositions object of the present invention could be liquid suitable for the oral and/or parental administration such as, for example, drops, syrups, solutions, injectable solutions ready to use or prepared by diluting a lyophilizate, but preferably solid or semi-solid such as tablets, capsules, granulates, powders, pellets, ovules, suppositories, creams, pomades, gels, ointments; or moreover solutions, suspensions, emulsions or other forms suitable for the administration by inhalatory and transdermic route.

The composition according to the present invention may comprise some solid or liquid excipients or diluents for pharmaceutical use and, if desired, other additives, usually used in the preparation of pharmaceutical compositions, such as, for example, thickeners, aggregating agents, lubricants, disgregating agents, aromatizing agents and colourings.

The pharmaceutical compositions object of the invention can be prepared according to usual techniques.

The $^1$H-NMR spectra were carried out in solutions of $CDCl_3$ or $d_6$-DMSO by using a Varian Gemini 200 MHz spectometer. The chemical shifts were reported in $\delta$ unity by using $CHCl_3$ or DMSO as inner standards.

The HPLC/MS analyses were carried out by using a Gilson instrument containing a Gilson Xterra RP18 column (5 μm, 4.6×50 mm) and by using as detector a diode array UV (220 nm), a Finnigan AQA mass spectrometer (electron spray, positive or negative ionization) and a ELSD detector.

Used conditions: flow speed: 1.2 ml/min; column temperature: 40° C.; elution gradient A/B (eluant A: 0.5% formic acid in water; eluant B: 0.5% formic acid in acetonitrile): t=0 min., A/B=95:5, t=8 min., A/B=5:95.

In order to better illustrate the present invention the following examples are now provided.

In the following table the chemical structures of synthetic intermediates and compounds of formula I are reported.

| Intermediates | Structure |
| --- | --- |
| intermediate a | 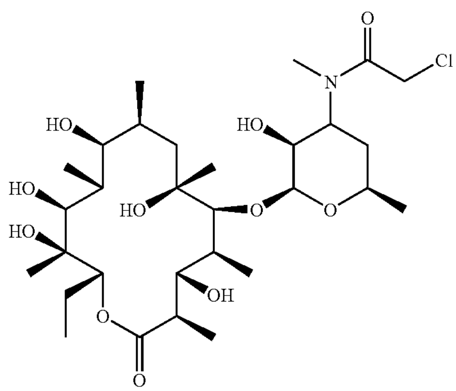 |
| intermediate b | 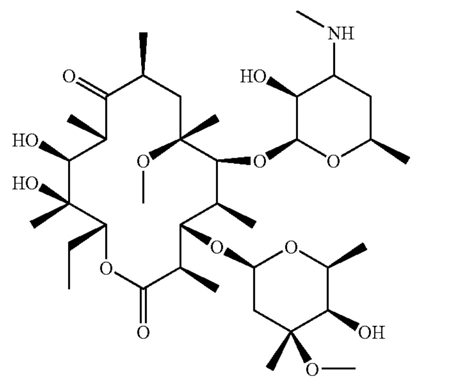 |
| intermediate c | 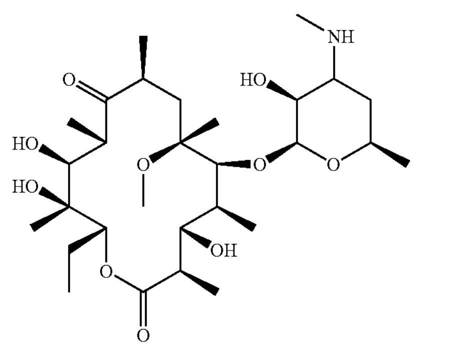 |
| intermediate d | 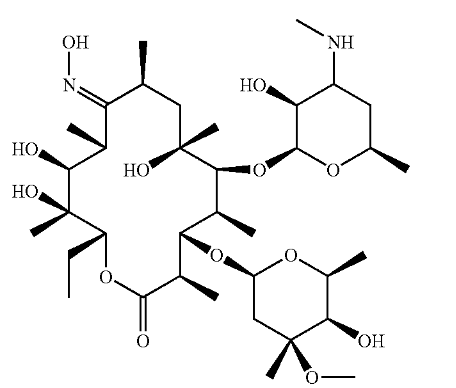 |

-continued
| | |
|---|---|
| intermediate e | 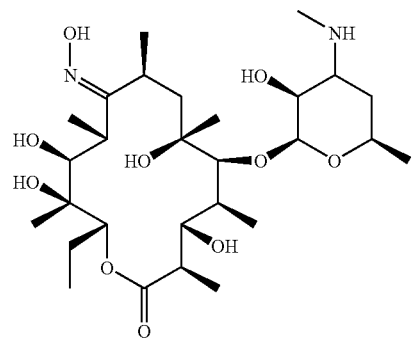 |
| Compounds | Structure |
|---|---|
| compound 1 | 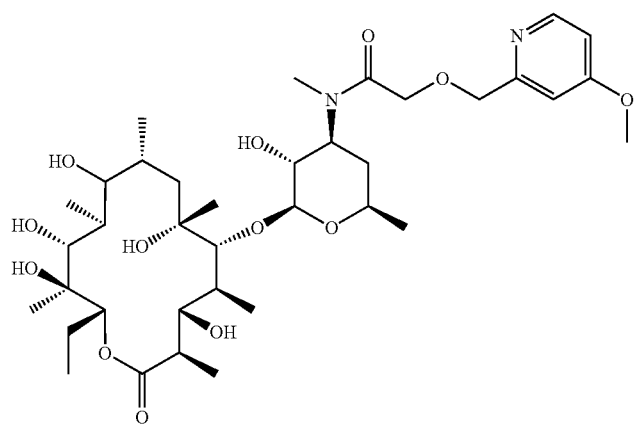 |
| compound 2 | 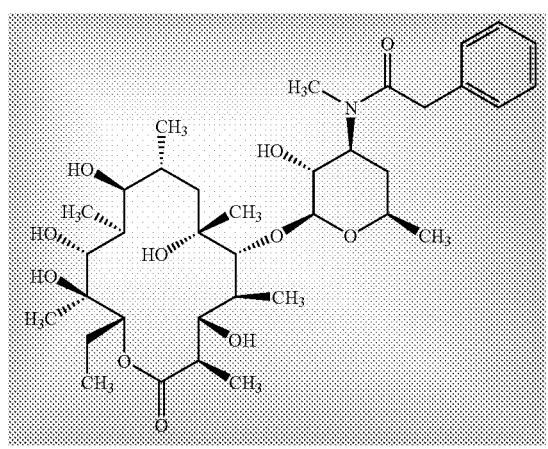 | compound 3
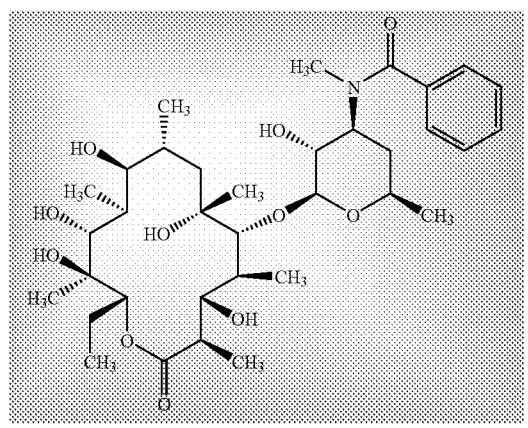
compound 4
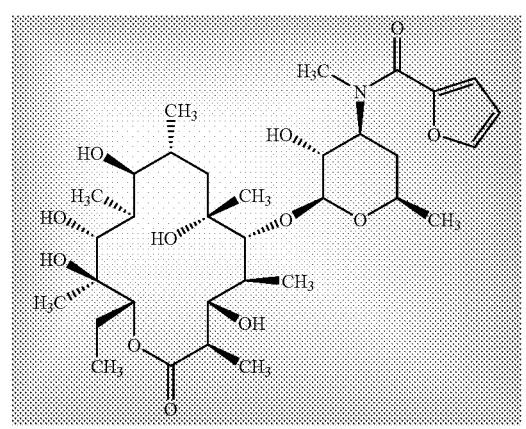
compound 5
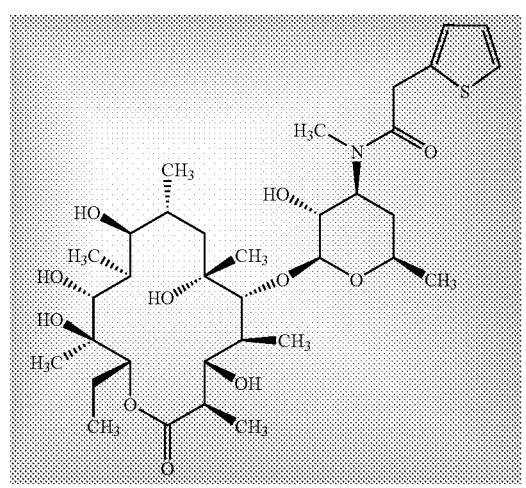

-continued
compound 6
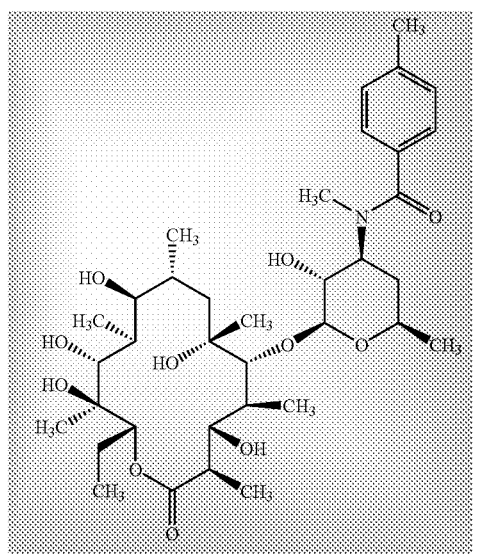
compound 7
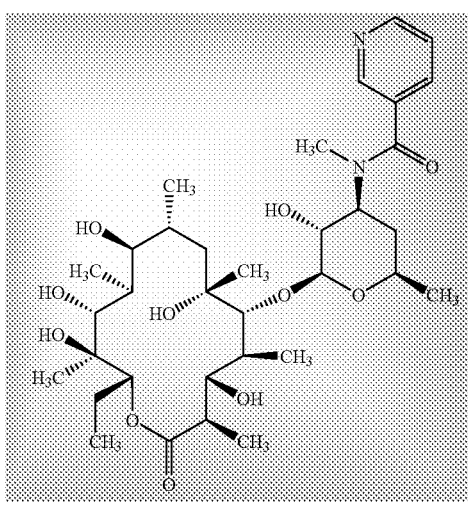
compound 12
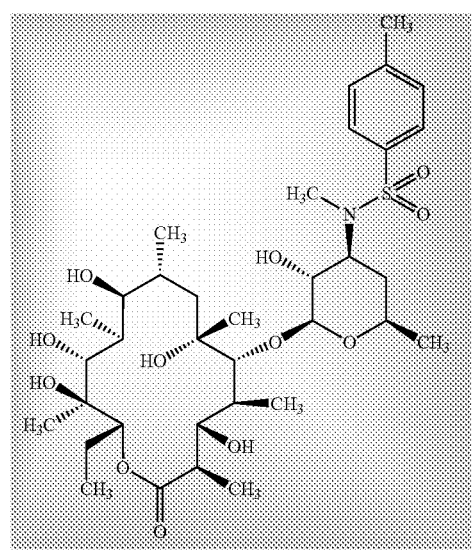

-continued
compound 8
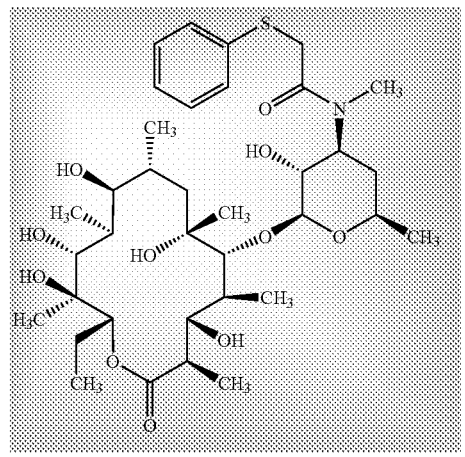
compound 19
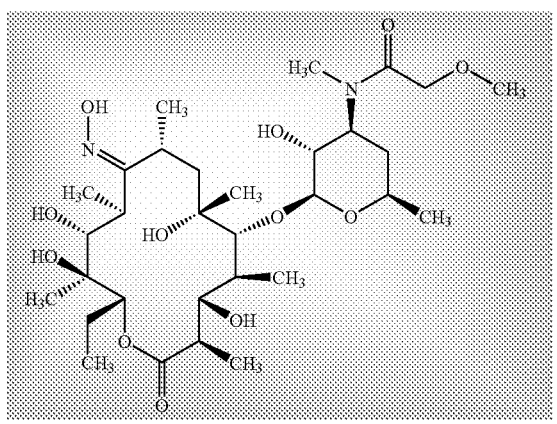
compound 26
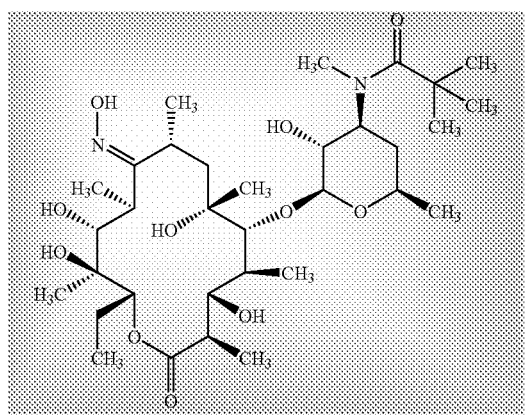

-continued
compound 20
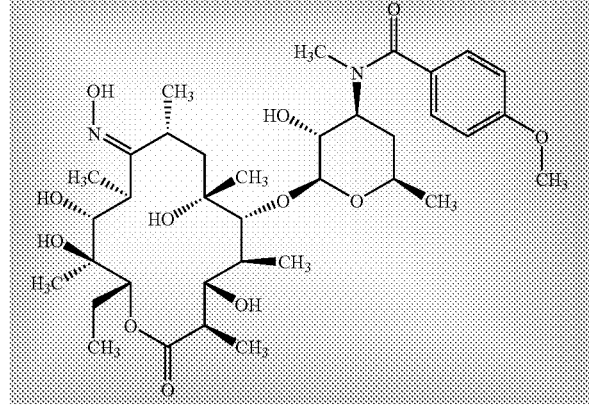
compound 22
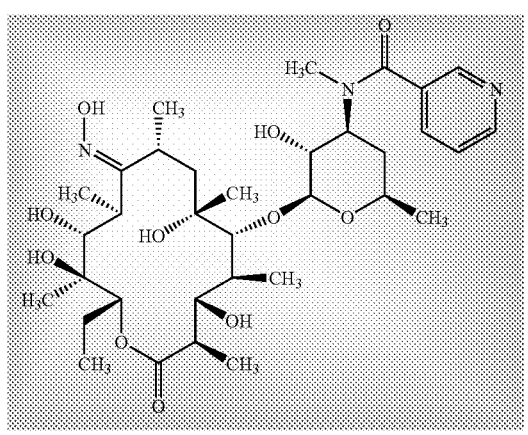
compound 23
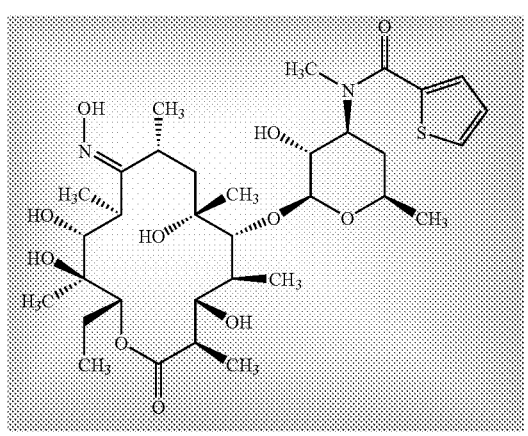

-continued
compound 11
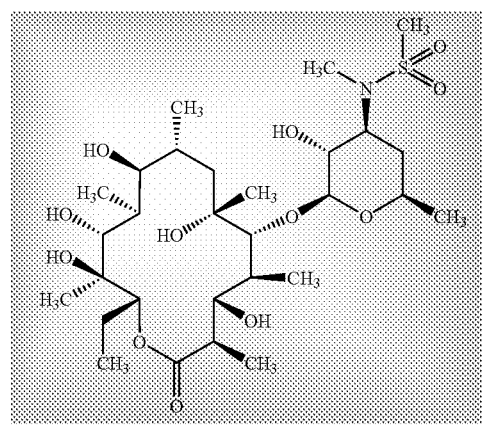
compound 9
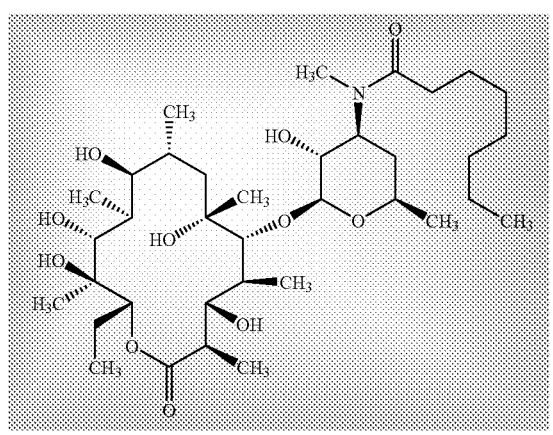
compound 27
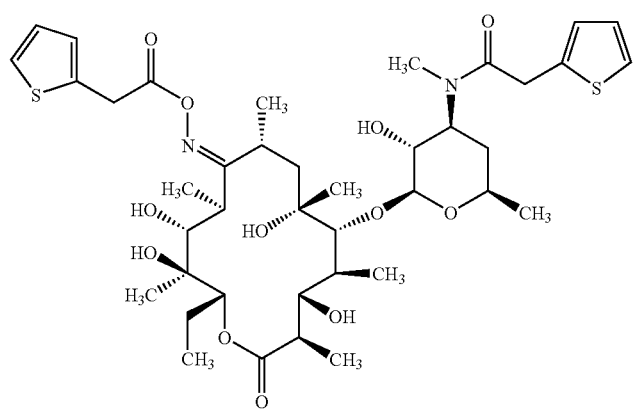

| | |
|---|---|
| compound 25 | 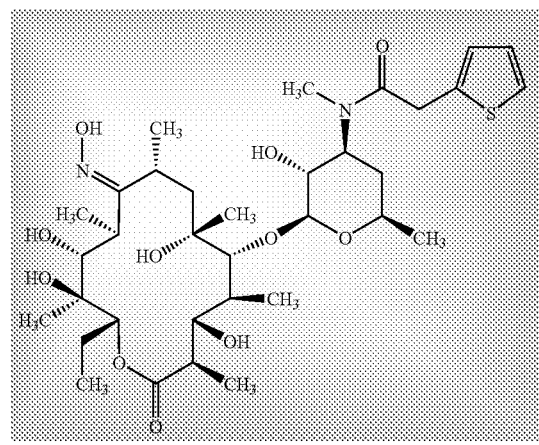 |
| compound 13 | 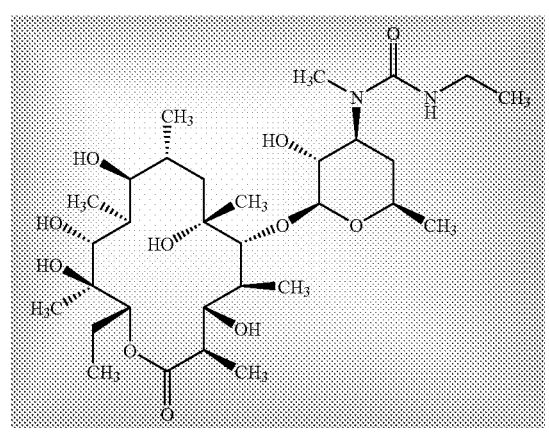 |
| compound 10 | 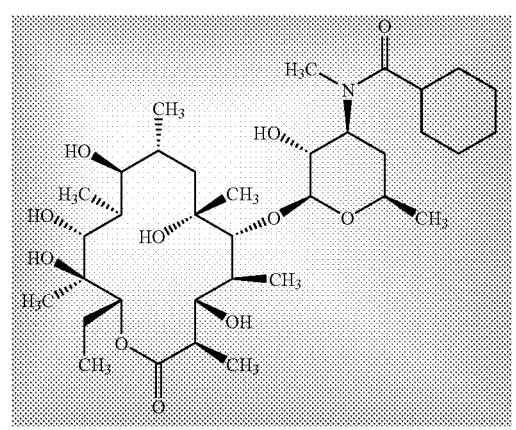 | compound 28
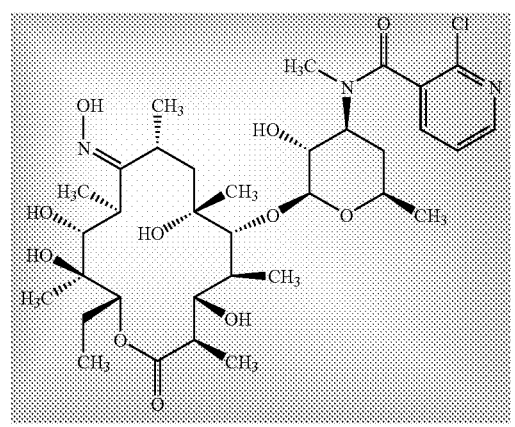
compound 14
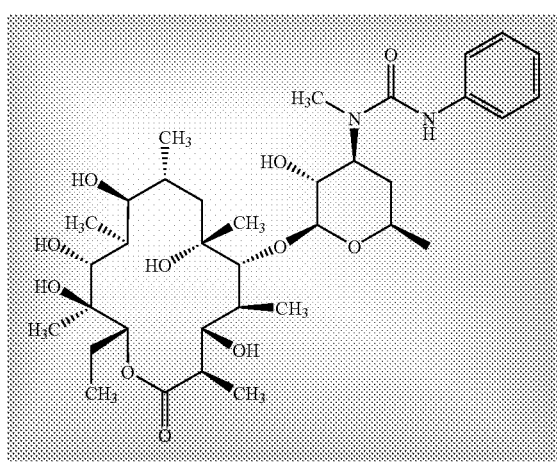
compound 15
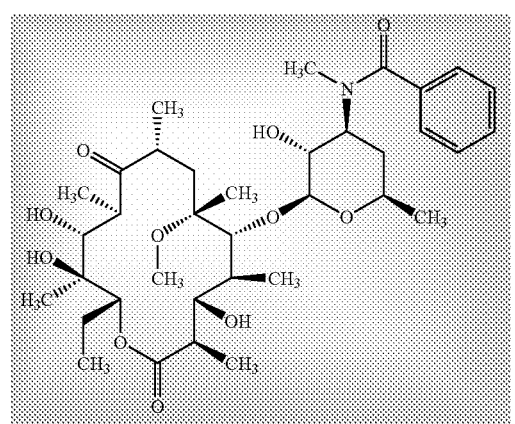

-continued
compound 29
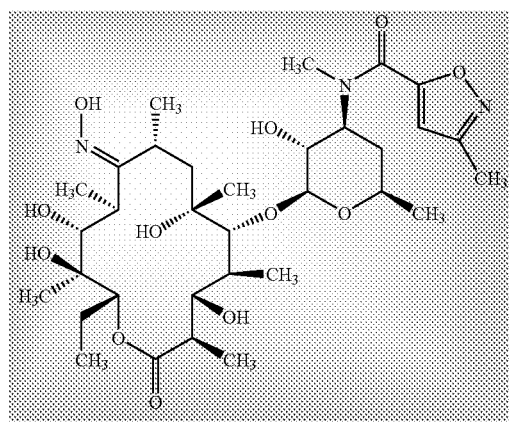
compound 16
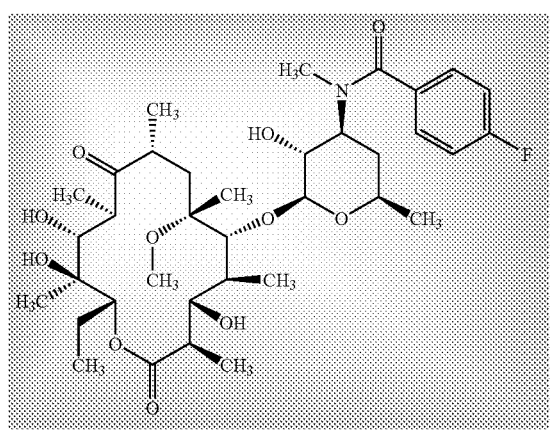
compound 18
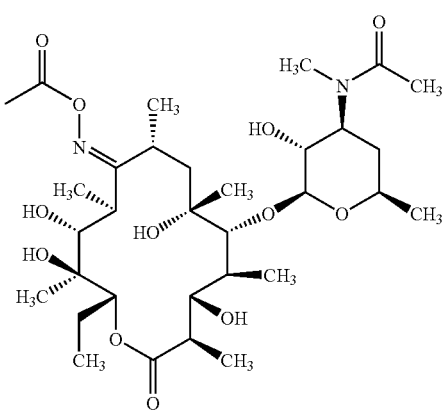

| | |
|---|---|
| compound 17 | 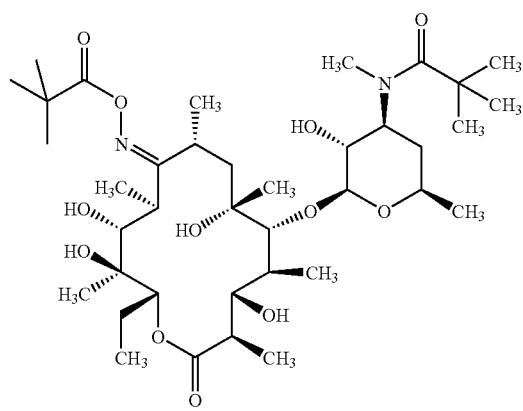 |
| compound 21 | 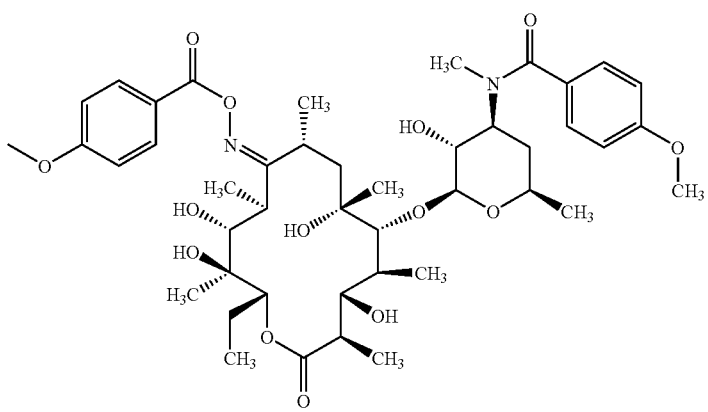 |
| compound 24 | 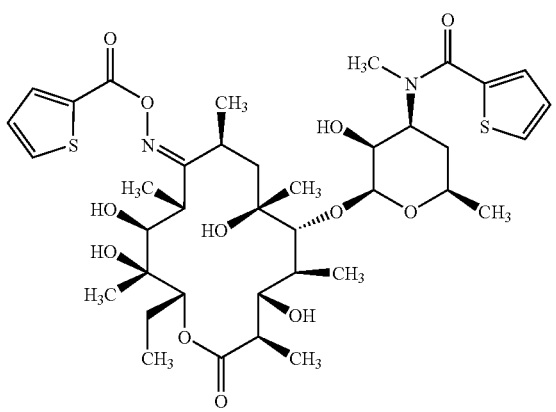 |

EXAMPLE 1

Preparation of Intermediate a

To a solution containing 3-O-descladinosyl-3'-desmethyl-9-dihydro-erythromycin A (463 mg, 0.82 mmol) compound, prepared as described in the co-pendending Italian patent application No. MI2002A001726 in the name of the same Applicant filed on 1 Aug. 2002 (intermediate 4) and chlorineacetic acid (85.4 mg, 0.904 mmol) in THF (10 ml), N-cyclohexylcarbodiimide resin, N-methyl polyester (1.2 g, 1.8 mmol/g) were added keeping under stirring for 24 hours. The solution was filtered by washing with acetonitrile and the obtained organic solution was dried to obtain intermediate a (0.427 g, 91% yield) which was directly utilized for the subsequent reaction.

$[M+1]^+$ 640.3 HPLC-ELSD: Rt=4.64; 84.3% ELSD purity

EXAMPLE 2

Preparation of Compound 1

To a suspension of NaH (80 mg, 60%, 2 mmol) in THF (10 ml) (4-methoxy-pyridin-2-yl)-methanol (278 mg, 2 mmol) was added and it was left to react for 45 min. A solution of intermediate a (0.427 mg, 0.67 mmol) in THF (5 ml) was quickly added and it was left to react for 16 hours. After acid-base washings, the obtained crude was purified by chromatography on Biotage (40M column, CH$_2$Cl$_2$/McOH/NH$_3$ 30/1/0.1 eluant) to give compound 1 (200 mg, 40% yield) as white solid.

[M+1]$^+$ 743.39 HPLC-ELSD: Rt=3.61; 95.2% ELSD purity $^1$H-NMR (DMSO_d6): 8.28, 6.99 and 6.86 (3m, 3H, pyridine); 4.52 (m, 1H, H$_1$'); 3.93 (s, 1H, H$_{11}$); 3.80 (s, 3H, CH$_3$O); 3.28 (s, 3H, MeN); 0.70 (t, 3H, J=7.2, H$_{15}$). TLC (CH$_2$Cl$_2$/MeOH/NH$_3$ 9/1/0.1) Rf=0.3.

EXAMPLE 3

Preparation of Compound 2

To a solution of 3-O-descladinosyl-3'-desmethyl-9-dihydro-erythromycin A (300 mg, 0.532 mmol) compound and triethylamine (110 μl, 0.784 mmol) in THF (3 ml), a solution of phenylacetyl chloride (71 μl, 0.532 mmol) in THF (1 ml) was added dropwise at a temperature of 0° C. and the resulting mixture was kept under stirring for 8 hours.

The reaction was processed by adding methanol and by evaporating the solvent under reduced pressure. The obtained crude was diluted with ethyl acetate (50 ml) and the organic phase was washed with HCl 2N (3×30 ml) and K$_2$CO$_3$ 10% (2×30 ml). The obtained organic solution was dried onto anhydrous Na$_2$SO$_4$, filtered and the solvent was evaporated under reduced pressure to give a solid which was purified by chromatography on Biotage (12M Cartridge column, CH$_2$Cl$_2$/MeOH 30/1 eluant). Compound 2 (217 mg, 60% yield) was obtained as white solid.

[M+1]$^+$=682.91; HPLC-ELSD: Rt=5.90 min; 100% ELSD purity $^1$H-NMR (CDCl$_3$): 7.3-7.2 (m, 5H, Ph); 3.82 (s, 1H, H$_{11}$); 2.85 (s, 3H, MeN); 2.66 (m, 2H, CH$_2$Ph); 0.87 (t, 3H, J=7.4, H$_{15}$). TLC (CH$_2$Cl$_2$/MeOH 9/1) Rf=0.6.

EXAMPLE 4

Preparation of Compound 3

To a solution of 3-O-descladinosyl-3'-desmethyl-9-dihydro-erythromycin A (66 mg, 0.117 mmol) compound and triethylamine (33 μl, 0.235 mmol) in CH$_2$Cl$_2$ (3 ml) a solution of benzoyl chloride (16.5 mg, 0.117 mmol) in CH$_2$Cl$_2$ (1 ml) was added dropwise at a temperature of 0° C. and the resulting mixture was kept under stirring for 8 hours.

The reaction mixture was diluted with ethyl acetate (50 ml) and the organic phase was washed with HCl 2N (3×30 ml), K$_2$CO$_3$ 10% (2×30 ml). The obtained organic phase was dried onto anhydrous Na$_2$SO$_4$, filtered and evaporated from the solvent to give compound 3 (55 mg, 70% yield) as white solid.

[M+1]$^+$=668.63; HPLC-ELSD: Rt=6.05 min; 97.0% ELSD purity $^1$H-NMR (CDCl$_3$): 7.3-7.2 (m, 5H, Ph); 4.54 (d, 1H, J=7.3, H$_1$'); 3.78 (s, 1H, H$_{11}$); 2.89 (s, 3H, MeN); 0.88 (t, 3H, J=7.1, H$_{15}$). TLC (CH$_2$Cl$_2$/MeOH 20/1) Rf=0.4.

EXAMPLE 5

Preparation of Compound 4

Compound 4 was synthetized from 3-O-descladinosyl-3'-desmethyl-9-dihydro-erythromycin A (300 mg, 0.532 mmol) and 2-furanyl chloride (70 mg, 0.532 mmol), following the procedure used to prepare compound 3. Compound 4 (315 mg, 90% yield) was obtained as white solid.

[M+1]$^+$ 658.57 HPLC-ELSD: Rt=5.48; 99.4% ELSD purity $^1$H-NMR (CDCl$_3$): 7.54 7.1 e 6.52 (3m, 3H, furan); 4.54 (d, 1H, J=7.4, H$_1$'); 4.5-4.4 (m, 1H, H$_{13}$); 3.88 (s, 1H, H$_{11}$); 3.15 (s, 3H, MeN); 0.90 (t, 3H, J=7.4, H$_{15}$). TLC (CH$_2$Cl$_2$/MeOH 10/1) Rf=0.5

EXAMPLE 6

Preparation of Compound 5

Compound 5 was synthetized from 3-O-descladinosyl-3'-desmethyl-9-dihydro-erythromycin A (300 mg, 0.532 mmol) and 2-thiophenacetyl chloride (85 mg, 0.53 mmol) following the procedure used to prepare compound 3. Compound 5 (269 mg, 74% yield) was obtained as white solid.

[M+1]$^+$ 688.62 HPLC-ELSD: Rt=5.96; 95.2% ELSD purity $^1$H-NMR (CDCl$_3$): 7.20 (m, 1H, thiophene); 6.9 (m, 2H, thiophene); 3.87 (s, 1H, H$_{11}$); 2.94 (s, 3H, MeN); 2.77 (m, 2H, CH$_2$CO); 0.90 (t, 3H, J=7.4, H$_{15}$). TLC (CH$_2$Cl$_2$/MeOH 10/1) Rf=0.5

EXAMPLE 7

Preparation of Compound 6

Compound 6 was synthetized from 3-O-descladinosyl-3'-desmethyl-9-dihydro-erythromycin A (300 mg, 0.532 mmol) and p-toluyl chloride (82 mg, 0.532 mmol) following the procedure used to prepare compound 3. Compound 6 (350 mg, 95% yield) was obtained as white solid.

[M+1]$^+$ 682.61 HPLC-ELSD: Rt=6.02; 99.9% ELSD purity $^1$H-NMR (CDCl$_3$): 7.35 (m, 2H, MePh); 7.35 (m, 2H, PhCO); 4.54 (m, 1H, H$_{13}$); 4.44 (d, 1H, J=7.4, H$_1$'); 3.86 (s, 1H, H$_{11}$); 2.91 (s, 3H, MeN); 2.38 (s, 3H, CH$_3$Ph); 0.90 (t, 3H, J=7.3, H$_{15}$). TLC (CH$_2$Cl$_2$/MeOH 10/1) Rf=0.5

EXAMPLE 8

Preparation of Compound 7

Compound 7 was synthetized from 3-O-descladinosyl-3'-desmethyl-9-dihydro-erythromycin A (300 mg, 0.532 mmol) and nicotyl chloride hydrochloride (94.7 mg, 0.532 mmol) following the procedure used to prepare compound 3. Purification of the obtained crude was carried out by chromatography on Biotage (12M Cartridge column, eluant CH$_2$Cl$_2$/MeOH 30/1) to give compound 7 (320 mg, 80% yield) as white solid.

[M+1]$^+$ 669.6 HPLC-ELSD: Rt=4.75; 99.0% ELSD purity $^1$H-NMR (CDCl$_3$): 8.8-8.9 (m, 2H, pyridine); 7.80 e 7.37 (2m, 2H, pyridine); 3.00 e 2.94 (2s, 3H, conformers MeN); 0.90 (t, 3H, J=7.3, H$_{15}$). TLC (CH$_2$Cl$_2$/MeOH 10/1) Rf=0.3

EXAMPLE 9

Preparation of Compound 8

Compound 8 was synthetized from 3-O-descladinosyl-3'-desmethyl-9-dihydro-erythromycin A (300 mg, 0.532 mmol) and phenyltioacetyl chloride (105 mg, 0.532 mmol) following the procedure used to prepare compound 3. Purification of the obtained crude was carried out by chromatography on Biotage (12M Cartridge column, CH$_2$Cl$_2$/MeOH 40/1 eluant) to give compound 8 (253 mg, 66% yield) as white solid.

[M+1]$^+$ 714.82 HPLC-ELSD: Rt=7.49; 97.0% ELSD purity; $^1$H-NMR (CDCl$_3$): 7.4.-7.5 (m, 2H, Ph); 7.2-7.35 (m, 2H, Ph); 4.60 (m, 1H, H$_{13}$); 4.50 (d, 1H, J=7.4, H$_1$'); 3.84 (s, 1H, H$_{11}$); 3.77 (m, 2H, CH$_2$S); 2.96 (s, 3H, MeN); 0.90 (t, 3H, J=7.3, H$_{15}$). TLC (CH$_2$Cl$_2$/MeOH 10/1)Rf=0.45

EXAMPLE 10

Preparation of Compound 9

Compound 9 was synthetized from 3-O-descladinosyl-3'-desmethyl-9-dihydro-erythromycin A (150 mg, 0.266 mmol) and octanoyl chloride (43 mg, 0.266 mmol) following the procedure used to prepare compound 3. Purification of the obtained crude was carried out by chromatography on Biotage (12M Cartridge column, $CH_2Cl_2$/MeOH 40/1 eluant) to give compound 9 (91 mg, 59% yield) as gummy white solid.

$[M+1]^+$ 690.82 HPLC-ELSD: Rt=6.94; 99.9% ELSD purity; $^1$H-NMR ($CDCl_3$): 4.50 (d, 1H, J=7.4, $H_1'$); 3.86 (s, 1H, $H_{11}$); 2.91 (s, 3H, MeN); 0.93-0.84 (m, 6H, $CH_3$ e $H_{15}$). TLC ($CH_2Cl_2$/MeOH 10/1) Rf=0.5

EXAMPLE 11

Preparation of Compound 10

Compound 10 was synthetized from 3-O-descladinosyl-3'-desmethyl-9-dihydro-erythromycin A (150 mg, 0.266 mmol) and cycloesanoyl chloride (39 mg, 0.266 mmol) following the procedure used to prepare compound 3. Purification of the obtained crude was carried out by chromatography on Biotage (12M Cartridge column, $CH_2Cl_2$/MeOH 40/1 eluant) to give compound 10 (150 mg, 86% yield) as white solid.

$[M+1]^+$ 674.7 HPLC-ELSD: Rt=5.98; 99.9% ELSD purity; $^1$H-NMR ($CDCl_3$): 4.53 (d, 1H, J=7.4, $H_1'$); 3.86 (s, 1H, $H_{11}$); 2.94 (s, 3H, MeN); 0.89 (t, 3H, J=7.3, $H_{15}$). TLC ($CH_2Cl_2$/MeOH 10/1) Rf=0.45

EXAMPLE 12

Preparation of Compound 11

Compound 11 was synthetized from 3-O-descladinosyl-3'-desmethyl-9-dihydro-erythromycin A (150 mg, 0.266 mmol) and metylsolfonyl chloride (31 mg, 0.266 mmol) following the procedure used to prepare compound 3. Compound 11 (112 mg, 67% yield) was obtained as white solid.

$[M+1]^+$ 642.57 HPLC-ELSD: Rt=5.46; 99.0% ELSD purity; $^1$H-NMR ($CDCl_3$): 4.57 (m, 1H, $H_{13}$); 4.44 (d, 1H, J=7.4, $H_1'$); 3.85 (s, 1H, $H_{11}$); 2.93 (s, 3H, MeN); 2.85 (s, 3H, $MeSO_2$); 0.90 (t, 3H, J=7.4, $H_{15}$). TLC ($CH_2Cl_2$/MeOH 10/1) Rf=0.5

EXAMPLE 13

Preparation of Compound 12

Compound 12 was synthetized from 3-O-descladinosyl-3'-desmethyl-9-dihydro-erythromycin A (300 mg, 0.532 mmol) and p-toluensolfonyl chloride (101 mg, 0.532 mmol), following the procedure used to prepare compound 3. Purification of the obtained crude was carried out by chromatography on Biotage (12M Cartridge column, $CH_2Cl_2$/MeOH 40/1 eluant) to give compound 12 (250 mg, 60% yield) as white solid.

$[M+1]^+$ 718.77 HPLC-ELSD: Rt=7.71; 97.2% ELSD purity $^1$H-NMR ($CDCl_3$): 7.75 (m, 2H, MePh); 7.35 (m, 2H, $PhSO_2$); 4.6-4.5 (m, 1H, $H_{13}$); 4.51 (d, 1H, J=7.3, $H_1'$); 3.88 (s, 1H, $H_{11}$); 2.77 (s, 3H, MeN); 2.43 (s, 3H, $CH_3Ph$); 0.90 (t, 3H, J=7.4, $H_{15}$). TLC ($CH_2Cl_2$/MeOH 10/1) Rf=0.5

EXAMPLE 14

Preparation of Compound 13

To a solution of 3-O-descladinosyl-3'-desmethyl-9-dihydro-erythromycin A (150 mg, 0.266 mmol) in $CH_2Cl_2$ (2 ml), a solution of ethyl isocyanate (18.9 mg, 0.266 mmol) was added dropwise at a temperature of 0° C. It was left to react at room temperature for 16 hours to be diluted, then, with ethyl acetate (30 ml) by washing with HCl 1N (3×20 ml) and $K_2CO_3$ 10% (2×20 ml). The organic phase was dried onto anhydrous $Na_2SO_4$, filtered and the solvent evaporated under reduced pressure. Purification of the obtained crude was carried out by chromatography on Biotage (12M Cartridge column, $CH_2Cl_2$/MeOH 40/1 eluant) to give compound 13 (120 mg, 70% yield) as white solid.

$[M+1]^+$ 674.7 HPLC-ELSD: Rt=4.93; 99.0% ELSD purity; $^1$H-NMR ($CDCl_3$): 4.9 (broad s, 1H, NHCO); 4.55 (m, 1H, $H_{13}$); 3.84 (s, 1H, $H_{11}$); 3.25 (m, 2H, $CH_2N$); 2.77 (s, 3H, MeN); 0.88 (t, 3H, J=7.3, $H_{15}$). TLC ($CH_2Cl_2$/MeOH 10/1) Rf=0.4

EXAMPLE 15

Preparation of Compound 14

Compound 14 was synthetized from 3-O-descladinosyl-3'-desmethyl-9-dihydro-erythromycin A (150 mg, 0.266 mmol) and phenyl isocyanate (31.7 mg, 0.266 mmol) following the procedure used to prepare compound 13. Compound 14 (175 mg, 95% yield) was obtained as white solid.

$[M+1]^+$ 683.62 HPLC-ELSD: Rt=6.21; 96.0% ELSD purity; $^1$H-NMR ($CDCl_3$): 7.25-7.36 (m, 3H, Ph); 7.0-7.1 (m, 2H, Ph); 4.55 (m, 1H, $H_{13}$); 4.25 (d, 1H, J=7.4, $H_1'$); 3.74 (s, 1H, $H_{11}$); 2.84 (s, 3H, MeN); 0.90 (t, 3H, J=7.3, $H_{15}$). TLC ($CH_2Cl_2$/MeOH 20/1) Rf=0.2

EXAMPLE 16

Preparation of Intermediate b

A suspension of clarithromycin (5 g, 6.7 mmol) in methanol (150 ml) was kept under light flow of $N_2$ and under mechanical stirring. Sodium acetate (0.66 g, 8 mmol) and iodine (2.03 g, 8 mmol) were added and the resulting mixture was subjected to the light of a 400-Watt lamp by making sure to keep the temperature between 10-20° C. through an ice-water bath.

After 6 h the solvent was evaporated under reduced pressure by re-taking the crude with 5% ethyl acetate and sodium metabisulfite in water by extracting the aqueous phase, which was then basified by adding ammonia by extracting then with dichloromethane. From the organic phase, after being dried onto anhydrous $Na_2SO_4$, filtered and evaporated from the solvent, a crude (5.1 g) was obtained which was purified by chromagraphy on Biotage (Silica 40M cartridge, $CH_2Cl_2$/MeOH/$NH_3$ eluant at first 100/3/0.3 and then 100/5/0.5) to give intermediate b (3.2 g, 4.36 mmol; 65% yield).

$[M+1]^+$=734.83; HPLC-ELDS: Rt=3.60 min; purity 99.9% $^1$H-NMR ($CDCl_3$) 5.05 (m, 1H, $H_{13}$); 4.92 (d, 2H, J=4.5, $H_1''$); 4.41 (d, 2H, J=7.5, $H_1'$); 3.98 (s, 1H, $H_{11}$); 3.32 (s, 3H, $H_7''$); 3.03 (s, 3H, $CH_3$ clarithro); 2.41 (s, 3H, MeN); 0.84 (t, 3H, J=7.4, $H_{15}$).

EXAMPLE 17

Preparation of Intermediate c

Intermediate b (2 g, 2.72 mmol) was dissolved into a 1 N solution of HCl (50 ml, 50 mmol) and kept under stirring for 2 hours at room temperature. The solution was basified with $NH_3$ conc. and then extracted with ethyl acetate (3×50 ml). The obtained organic phase was dried onto anhydrous $Na_2SO_4$, filtered and evaporated from the solvent to give intermediate c (1.56 g, 90% yield).

$[M+1]^+$=576.48; HPLC-ELSD: Rt=2.80 min; 98% ELSD purity. $^1$H-NMR (CDCl$_3$): 5.17 (m, 1H, H$_{13}$); 4.41 (d, 2H, J=8.1, H$_1$'); 2.96 (s, 3H, CH$_3$ clarithro); 2.42 (s, 3H, MeN); 0.83 (t, 3H, J=7.5, H$_{15}$).

EXAMPLE 18

Preparation of Compound 15

Compound 15 was synthetized from intermediate c (180 mg, 0.311 mmol) and benzoyl chloride (43.7 mg, 0.311 mmol) following the procedure used to prepare compound 3. Purification of the obtained crude was carried out by chromatography on silica (Varian Mega-bond Elut column, eluant from CH$_2$Cl$_2$ to CH$_2$Cl$_2$/MeOH 25/1) to give compound 15 (91 mg, 59% yield) as white solid.

$[M+1]^+$ 682.58 HPLC-ELSD: Rt=5.86; 99.9% ELSD purity; $^1$H-NMR (CDCl$_3$): 7.4 (m, 5H, Ph); 5.16 (m, 1H, H$_{13}$); 4.55 (d, 1H, J=7.0, H$_1$'); 3.92 (s, 1H, H$_{11}$); 2.96 (s, 3H, CH$_3$ clarithro); 2.90 (s, 3H, MeN); 0.83 (t, 3H, J=7.4, H$_{15}$). TLC (CH$_2$Cl$_2$MeOH 20/1) Rf=0.3

EXAMPLE 19

Preparation of Compound 16

Compound 16 was synthetized from intermediate c (180 mg, 0.311 mmol) and 4-fluorinebenzoyl chloride (49.6 mg, 0.311 mmol) following the procedure used to prepare compound 3. Purification of the obtained crude was carried out by chromatography on silica (Varian Mega-bond Elut column, eluant from CH$_2$Cl$_2$ to CH$_2$Cl$_2$/MeOH 25/1) to give compound 16 (130 mg, 60% yield) as white solid.

$[M+1]^+$ 697.5 HPLC-ELSD: Rt=6.01; 99.9% ELSD purity; $^1$H-NMR (CDCl$_3$): 7.49-7.41 (m, 2H, F-Ph); 7.14-7.04 (m, 2H, PhCO); 5.17 (m, 1H, H$_{13}$); 4.55 (d, 1H, J=7.1, H$_1$'); 3.93 (s, 1H, H$_{11}$); 2.96 (s, 3H, CH$_3$ clarithro); 2.90 (s, 3H, MeN); 0.83 (t, 3H, J=7.3, H$_{15}$). TLC (CH$_2$Cl$_2$/MeOH 20/1) Rf=0.3

EXAMPLE 20

Preparation of Intermediate d

To a homogeneous solution of erythromycin A oxime (7.49 g, 10 mmol) in acetone (150 ml, anhydrified onto 3 Å molecular sieves), a solution of diethylazadicarboxylate (1.8 ml, 1.05 mmol) in acetone (5 ml) was added dropwise. The solution was left to react for 24 hours at room temperature, then the solvent was evaporated under reduced pressure by re-taking the obtained crude with NH$_4$Cl 5N in H$_2$O (3 ml) and by leaving to react for 1 hour to basify then with K$_2$CO$_3$ 10% (200 ml) and to extract with ethyl acetate (3×200 ml). The obtained organic phase was dried onto anhydrous Na$_2$SO$_4$, filtered and evaporated from the solvent. After purification by means of chromatography on Biotage (40M column, CH$_2$Cl$_2$/MeOH/NH$_3$ 95/5/0.5 eluant) intermediate d (5.5 g, 75% yield) was obtained.

$[M+1]^+$ 735.77 HPLC-ELSD: Rt=4.31; 99.0% purity $^1$H-NMR (CDCl$_3$): 7.6-8.4 (broad s, 1H, =N—OH); 5.07 (m, 1H, H$_{13}$); 4.91 (d, 1H, J=4.2, H$_1$'); 4.37 (d, 1H, J=7.4, H$_1$'); 3.30 (s, 3H, H$_7$"); 2.40 (s, 3H, MeN); 1.51 (s, 3H, H$_{18}$); 0.84 (m, 3H, H$_{15}$). TLC (CH$_2$Cl$_2$/MeOH/NH$_3$ 90/10/1) Rf=0.35

EXAMPLE 21

Preparation of Intermediate e

To a solution of intermediate d (4.65 mg, 6.33 mmol) in methanol (130 ml) 37% hydrochloric acid (2.2 ml) was added dropwise and the resulting mixture was kept under stirring for 2 hours. It was brought to pH=7 with NH$_3$ 30% (2.5 ml) and the solvent was removed under reduced pressure. The obtained crude was purified by chromatography on Biotage (40M Cartridge column, CH$_2$Cl$_2$/MeOH/NH$_3$ 95/5/0.5 eluant). Intermediate e (3.2 g, ELSD purity, 88% yield) was obtained as white solid.

$[M+1]^+$ 577.57 HPLC-ELSD: Rt=3.51; 99.0% purity $^1$H-NMR (CDCl$_3$): 5.17 (m, 1H, H$_{13}$); 4.44 (d, 1H, J=7.6, H$_1$'); 3.71 (s, 1H, H$_{11}$); 2.39 (s, 3H, MeN); 1.44 (s, 3H, H$_{18}$); 0.8-0.9 (m, 3H, H$_{15}$). TLC (CH$_2$Cl$_2$/MeOH/NH$_3$ 90/10/1) Rf=0.25

EXAMPLE 22

Preparation of Compound 17

To a solution of intermediate e (100 mg, 0.174 mmol) and triethylamine (49 µl, 0.35 mmol) in CH$_2$Cl$_2$ (3 ml) pivaloyl chloride (23.0 mg, 0.191 mmol) was added dropwise and the resulting mixture was kept under stirring for 2 hours. The reaction mixture was diluted with ethyl acetate (50 ml) and the organic phase was washed with HCl 2N (3×30 ml), K$_2$CO$_3$ 10% (2×30 ml), dried onto anhydrous Na$_2$SO$_4$, filtered and evaporated from the solvent. After purification by chromatography on silica (Varian Mega-bond Elut column, CH$_2$Cl$_2$/MeOH 98/2 eluant) compound 17 (50 mg, 46% yield) was obtained as white solid.

$[M+1]^+$ 745.81 HPLC-ELSD: Rt=6.56; 98.0% purity $^1$H-NMR (CDCl$_3$): 5.24 (m, 1H, H$_{13}$); 4.45 (d, 1H, J=7.2, H$_1$'); 3.79 (s, 1H, H$_{11}$); 3.00 (s, 3H, MeN); 1.41 (s, 3H, H$_{18}$); 1.29 (s, 9H, $^t$BuCO—N); 1.24 (s, 9H, $^t$BuCO—O); 0.80-0.88 (m, 3H, H$_{15}$).

EXAMPLE 23

Preparation of Compound 18

Compound 18 was synthetized from intermediate e (170 mg, 0.295 mmol) and acetyl chloride (28 mg, 0.350 mmol), following the procedure used to prepare compound 17. After purification by chromatography on silica (CH$_2$Cl$_2$/MeOH 95/5 eluant) compound 18 (100 mg, 51% yield) was obtained as white solid.

$[M+1]^+$ 661.68 HPLC-ELSD: Rt=4.90; 96.0% purity $^1$H-NMR (CDCl$_3$): 5.35 (m, 1H, H$_{13}$); 4.37 (d, 1H, J=7.2, H$_1$'); 3.81 (s, 1H, H$_{11}$); 3.00 (s, 3H, MeN); 2.15 (s, 3H, CH$_3$CO—N); 2.11 (s, 3H, CH$_3$CO—O); 1.48 (s, 3H, H$_{18}$); 0.79-0.87 (m, 3H, H$_{15}$).

EXAMPLE 24

Preparation of Compound 19

Compound 19 was synthetized from intermediate e (110 mg, 0.191 mmol) and methoxyacetyl chloride (23.5 mg, 0.21 mmol), following the procedure used to prepare compound 17. After purification by chromatography on silica (Varian Mega-bond Elut 5 g column, $CH_2Cl_2$/MeOH 98/2 eluant) compound 19 (20 mg, 16% yield) was obtained as white solid.

[M+1]$^+$ 649.58 HPLC-ELSD: Rt=4.78; 99.9% purity
$^1$H-NMR (CDCl$_3$): 5.21 (m, 1H, H$_{13}$); 4.50 (d, 1H, J=7.4, H$_1$'); 3.69 (s, 1H, H$_{11}$); 3.42 (s, 3H, CH$_3$O); 2.90 (s, 3H, MeN); 1.45 (s, 3H, H$_{18}$); 0.83 (t, 3H, J=7.4, H$_{15}$).

EXAMPLE 25

Preparation of Compound 20

Compound 20 was synthetized from intermediate e (100 mg, 0.173 mmol) and p-anisyl chloride (29.6 mg, 0.173 mmol), following the procedure used to prepare compound 17. After purification by chromatography on silica (Varian Mega-bond Elut 5 g column, $CH_2Cl_2$MeOH 98/2 eluant) compound 20 (70 mg, 57% yield) was obtained as white solid.

[M+1]$^+$ 711.72 HPLC-ELSD: Rt=5.82; 99.9% purity
$^1$H-NMR (CDCl$_3$): 7.8-8.6 (broad s, 1H, =N—OH); 7.42 (m, 2H, MeOPh); 6.90 (m, 2H, PhCO); 5.20 (m, 1H, H$_{13}$); 3.83 (s, 3H, CH$_3$O); 3.69 (s, 1H, H$_{11}$); 2.93 (s, 3H, MeN); 1.46 (s, 3H, H$_{18}$); 0.78-0.88 (m, 3H, H$_{15}$).

EXAMPLE 26

Preparation of Compound 21

Compound 21 was synthetized from intermediate e (110 mg, 0.191 mmol) and p-anisyl chloride (35 mg, 0.2 mmol), following the procedure used to prepare compound 17. After purification by chromatography on silica (Varian Mega-bond Elut 5 g column, $CH_2Cl_2$/MeOH 98/2 eluant) compound 21 (80 mg, 55% yield) was obtained as white solid.

[M+1]$^+$ 845.88 HPLC-ELSD: Rt=5.78; 99% purity
$^1$H-NMR (CDCl$_3$): 8.01 (m, 2H, MeOPh'); 7.40 (m, 2H, MeOPh); 6.95 (m, 2H, Ph'CO—O); 6.88 (m, 2H, PhCO—N); 5.28 (m, 1H, H$_{13}$); 3.88 (s, 3H, CH$_3$OPh'); 3.83 (s, 3H, CH$_3$OPh); 2.91 (s, 3H, MeN); 0.85 (m, 3H, H$_{15}$).

EXAMPLE 27

Preparation of Compound 22

Compound 22 was synthetized from intermediate e (100 mg, 0.173 mmol) and nicotyl chloride hydrochloride (36 mg, 0.173 mmol), following the procedure used to prepare compound 17. After purification by chromatography on silica (Varian Mega-bond Elut 5 g column, $CH_2Cl_2$/MeOH 98/2 eluant) compound 22 (60 mg, 51% yield) was obtained as white solid.

[M+1]$^+$ 682.58 HPLC-ELSD: Rt=5.78; 96% purity
$^1$H-NMR (DMSO_d6): 10.62 (broad s, 1H, =N—OH); 8.54-8.59 (m, 2H, pyridine); 7.75-7.80 (m, 1H, pyridine); 7.44-7.47 (m, 1H, pyridine); 5.05 (m, 1H, H$_{13}$); 3.88 (s, 1H, H$_{11}$); 2.85 (s, 3H, MeN).

EXAMPLE 28

Preparation of Compound 23

Compound 23 was synthetized from intermediate e (200 mg, 0.347 mmol) and 2-thiophencarbonyl chloride (35 mg, 0.347 mmol), following the procedure used to prepare compound 17. After purification by chromatography on silica (Varian Mega-bond Elut 5 g column, $CH_2Cl_2$/MeOH 98/2 eluant) compound 23 (100 mg, 42% yield) was obtained as white solid.

[M+1]$^+$ 687.61 HPLC-ELSD: Rt=5.78; 98% purity
$^1$H-NMR (DMSO_d6): 10.63 (broad s, 1H, =N—OH); 7.70, 7.41 and 7.08 (3m, 3H, thiophen); 5.14 (m, 1H, H$_{13}$); 4.40 (d, 1H, J=7.3, H$_1$'), 3.57 (s, 1H, H$_{11}$); 2.92 (s, 3H, MeN); 0.71 (t, 3H, J=7.3, H$_{15}$).

EXAMPLE 29

Preparation of Compound 24

Compound 24 was synthetized from intermediate e (200 mg, 0.347 mmol) and 2-thiophencarbonyl chloride (102 mg, 0.694 mmol), following the procedure used to prepare compound 17. After purification by chromatography on silica (Varian Mega-bond Elut 5 g column, $CH_2Cl_2$/MeOH 98.5/1.5 eluant) compound 24 (150 mg, 54% yield) was obtained as white solid.

[M+1]$^+$ 797.61 HPLC-ELSD: Rt=6.66; 98% purity
$^1$H-NMR (DMSO_d6): 7.99, 7.88, 7.70, 7.41, 7.26 and 7.09 (6m, 6H, 2 thiophen); 5.22 (m, 1H, H$_{13}$); 4.36 (d, 1H, J=7.3, H$_1$'); 2.91 (s, 3H, MeN); 0.72 (t, 3H, J=7.4, H$_{15}$).

EXAMPLE 30

Preparation of Compound 25

Compound 25 was synthetized from intermediate e (200 mg, 0.347 mmol) and 2-thiophenacethyl chloride (55.7 mg, 0.347 mmol), following the procedure used to prepare compound 17. After purification by chromatography on silica (Varian Mega-bond Elut 5 g column, $CH_2Cl_2$/MeOH 98/2 eluant) compound 25 (80 mg, 33% yield, 95% purity) was obtained as white solid.

[M+1]$^+$ 701.62 HPLC-ELSD: Rt=5.84; 98% purity

EXAMPLE 31

Preparation of Compound 26

Compound 26 was synthetized from intermediate c (200 mg, 0.347 mmol) and pivaloyl chloride (36.2 mg, 0.30 mmol), following the procedure used to prepare compound 3. After purification by chromatography on silica ($CH_2Cl_2$/MeOH eluant at first 99/1 then 98/2) compound 26 (33 mg, 17% yield) was obtained as white solid.

[M+1]$^+$ 661.65 HPLC-ELSD: Rt=5.90; 99.1% purity
$^1$H-NMR (CDCl$_3$): 5.20 (m, 1H, H$_{13}$); 4.47 (d, 1H, J=7.3, H$_1$'); 3.70 (s, 1H, H$_{11}$); 2.99 (s, 3H, MeN); 1.46 (s, 3H, H$_{18}$); 1.29 (s, 9H, $^t$Bu); 0.80-0.92 (m, 3H, H$_{15}$).

EXAMPLE 32

Preparation of Compound 27

Compound 27 (35 mg, 13% yield) was obtained and isolated during the synthesis and purification of compound 25.

[M+1]$^+$ 825.71 HPLC-ELSD: Rt=6.76; 96% purity
$^1$H-NMR (CDCl$_3$): 7.15-7.25 ((m, 2H, thiophen); 6.87-7.00 (m, 4H, thiophen); 5.25 (m, 1H, H$_{13}$); 4.43 (d, 1H, J=7.2, H$_1$'); 3.95 (m, 4H, 2CH$_2$CO); 3.79 (s, 1H, H$_{11}$); 2.97 (s, 3H, MeN); 0.8-0.9 (m, 3H, H$_{15}$).

EXAMPLE 33

Preparation of Compound 28

Compound 28 was synthetized from intermediate e (200 mg, 0.347 mmol) and 2-chlorinenicotyl chloride (61 mg, 0.347 mmol), following the procedure used to prepare compound 17. After purification by chromatography on silica (Varian Mega-bond Elut 5 g column, CH$_2$Cl$_2$/MeOH 99/1 eluant) compound 28 (100 mg, 40% yield) was obtained as white solid.

[M+1]$^+$ 716.65 HPLC-ELSD: Rt=5.40; 95% purity
$^1$H-NMR (CDCl$_3$): 8.42, 7.60 and 7.31 (3m, 3H, pyridine); 5.19 (m, 1H, H$_{13}$); 4.50 (d, 1H, J=7.3, H$_1$'); 2.91 (s, 3H, MeN).

EXAMPLE 34

Preparation of Compound 29

Compound 29 was synthetized from intermediate e (200 mg, 0.347 mmol) and 3-methyl-isoxazol-5-carbonyl chloride (44 mg, 0.347 mmol), following the procedure used to prepare compound 17. After purification by chromatography on silica (Varian Mega-bond Elut 5 g column, CH$_2$Cl$_2$/MeOH 99/1 eluant) compound 29 (130 mg, 63% yield) was obtained as white solid.

[M+1]$^+$ 689.59 HPLC-ELSD: Rt=5.44; 98% purity
$^1$H-NMR (CDCl$_3$): 7.25 (s, 1H, oxazole); 5.19 (m, 1H, H$_{13}$); 4.46 (d, 1H, J=7.3, H$_1$'); 3.16 (s, 3H, MeN); 2.44 (s, 3H, CH$_3$-ossaz.); 0.86 (t, 3H, J=7.3, H$_{15}$).

EXAMPLE 35

In Vivo Pharmacological Activity:
A) Acute contact dermatitis.
Animals:
Groups of 5 CD1 mice (18-24 g) were used.
Administration of the compounds:
All the macrolide derivatives were dissolved in the Transphase Delivery System (TPDS) vehicle containing 10% benzyl alcohol, 40% acetone and 50% isopropanol.

15 microliters of the compounds (500 μg/ear), dissolved in TPDS, were applied topically onto the inner surface of an ear; after 30 minutes 12 microliters of a solution of acetate of tetradecanoyl-phorbol (TPA) with the concentration of 0.01% dissolved in acetone were applied onto the same area.

After six hours the animals were sacrified by inhalation of CO$_2$.

Evaluation of the results:
The oedema level was calculated by detracting the weight of a defined portion of auricular ala of the not treated ear to the one of the treated controlateral ear. To determine the oedema remission level the weight difference of the groups treated with TPA+macrolides was compared with the ones of those treated with TPA only. The activity of the macrolides was measured by using the modified method of Zunic et coll. (1998): MDL (Lysyl) GDP, a non-toxil muramyl dipeptide derivative inhibits, cytokine production by activated macrophages and protects mice from phorbol ester-and oxazolone-induced inflammation (J. Invest Dermatol., 111 (1), 77-82).

The data relating to erythromycin concern the treatment in single dose with 500 μg/ear.

Results obtained with the compounds of formula I are reported in the following table.

| Compound | Oedema (% inhibition) |
|---|---|
| Erythromycin | 42.5 |
| Azithromycin | 40.0 |
| 1 | 61.5 |
| 2 | 88.1 |
| 3 | 89.9 |
| 4 | 64.4 |
| 5 | 53.7 |
| 6 | 77.8 |
| 7 | 46.1 |
| 8 | 57.6 |
| 9 | 74.2 |
| 10 | 89.2 |
| 11 | 55.3 |
| 12 | 72.2 |
| 13 | 80.3 |
| 14 | 89.9 |
| 15 | 74.3 |
| 16 | 81.1 |
| 17 | 51.2 |
| 18 | 49.0 |
| 19 | 86.1 |
| 20 | 83.2 |
| 21 | 53.3 |
| 22 | 74.3 |
| 23 | 86.8 |
| 24 | 41.3 |
| 25 | 79.3 |
| 27 | 61.4 |
| 28 | 81.7 |
| 29 | 74.1 |
| 26 | 68.6 |

The invention claimed is:

1. A compound of formula

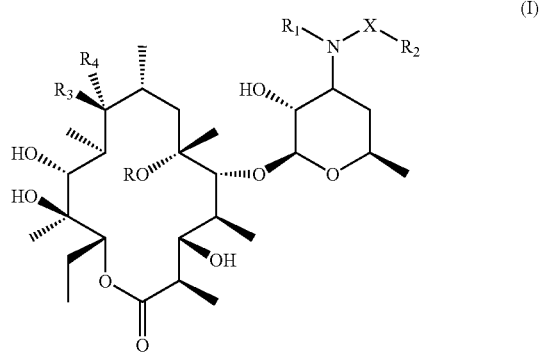

(I)

wherein
X is a —C(=O)—, —C(=O)—O—, —C(=O)—N—, —SO$_2$— or —SO$_2$—N group;
R is a hydrogen atom or methyl;
R$_1$ is a hydrogen atom or a (C$_1$-C$_3$)-alkyl group;
R$_2$ is a hydrogen atom, a (C$_1$-C$_4$)-alkoxy-(C$_1$-C$_4$)-alkyl group, a (C$_5$-C$_7$)-cycloalkyl group, a phenyl or a five- or six-membered heteroaryl having from one to three heteroatoms selected among nitrogen, oxygen and sulphur, a phenyl-(C$_1$-C$_4$)-alkyl or heteroaryl-(C$_1$-C$_4$)-alkyl group optionally substituted by 1 to 3 substituents selected among a (C$_1$-C$_4$)-alkyl group, a (C$_1$-C$_4$)-alkoxy group and halogen, or a chain of formula —(CH$_2$)$_r$—Y—(CH$_2$)$_m$-A wherein
A is a phenyl or a five- or six-membered heteroaryl having from one to three heteroatoms selected among nitrogen, oxygen and sulphur, both ones optionally substituted by 1 to 3 substituents selected among a $(C_1-C_4)$-alkyl group, a $(C_1-C_4)$-alkoxy group or halogen;

Y represents O, S or $NR_6$ wherein $R_6$ is a hydrogen atom, a linear or branched $(C_1-C_3)$ alkyl, a $(C_1-C_3)$-alkoxycarbonyl group or a benzyloxycarbonyl group;

r is an integer from 1 and 3;

m is an integer from 0 and 3;

$R_3$ is a hydroxy group or $R_3$ taken together with $R_4$ forms a (=O) group or a =N—O—$R_5$ group wherein $R_5$ is a hydrogen atom, a $(C_1-C_4)$-alkyl group, a benzyl or a —X—$R_2$ group wherein X and $R_2$ have the corresponding meanings defined above;

$R_4$ is a hydrogen atom or $R_4$ taken together with $R_3$ forms a (=O) group or a =N—O—$R_5$ group wherein $R_5$ has the meanings defined above;

and furthermore $R_2$ is a $(C_1-C_{10})$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$;

and pharmaceutically acceptable salts thereof.

2. A compound according to claim 1 wherein R, $R_1$, $R_2$ have the meanings as defined in formula I, X is a —C(=O)—, —C(=O)—N— or —$SO_2$— group and $R_3$ is a hydroxy group or $R_3$ taken together with $R_4$ forms a (=O) group or a =N—O—$R_5$ group wherein $R_5$ is a hydrogen atom, methyl, benzyl or a —X—$R_2$ group wherein X and $R_2$ have the meanings as defined in formula I.

3. A compound according to claim 2 wherein $R_1$ is a hydrogen atom or methyl and $R_5$ is a hydrogen atom or a —X—$R_2$ group wherein X and $R_2$ have the meanings as defined in formula I.

4. A compound according to claim 3 wherein $R_2$ is a hydrogen atom, a $(C_1-C_4)$-alkoxy-$(C_1-C_4)$-alkyl group, a $(C_5-C_7)$-cycloalkyl group, a phenyl or a five- or six-membered heteroaryl having from one to three heteroatoms selected among nitrogen, oxygen and sulphur, a phenyl-$(C_1-C_4)$-alkyl or heteroaryl-$(C_1-C_4)$-alkyl group optionally substituted by 1 to 3 substituents selected among a $(C_1-C_4)$-alkyl group, a $(C_1-C_4)$-alkoxy group or halogen, or a chain to formula

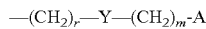

wherein

A is a phenyl or a heteroaryl selected among furan, thiophene, oxazole, imidazole, pyridine, pyrimidine and triazole both ones optionally substituted by 1 to 3 substituents selected among a $(C_1-C_4)$-alkyl group, a $(C_1-C_4)$-alkoxy group or halogen;

Y represents O, S or $NR_6$ wherein $R_6$ is a hydrogen atom or methyl;

r is an integer from 1 and 3;

m is an integer from 0 and 3;

and furthermore $R_2$ is a $(C_1-C_{10})$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

5. A compound according to claim 1 wherein $R_1$ is methyl and $R_2$ is a metoxy-$(C_1-C_3)$-alkyl group, a $(C_5-C_7)$-cycloalkyl group, a phenyl or a heteroaryl selected among furan, thiophene, oxazole and pyridine, a benzyl or heteroaryl-$(C_1-C_4)$-alkyl group optionally substituted by a substituent selected among a $(C_1-C_4)$-alkyl group, a metoxy group and halogen, or a chain of formula

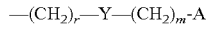

wherein

A is a phenyl or a heteroaryl selected among furan, thiophene, oxazole and pyridine, both ones optionally substituted by a substituent selected among a $(C_1-C_4)$-alkyl group, a metoxy group or halogen;

Y represents O, S or $NR_6$ wherein $R_6$ is a hydrogen atom;

r is an integer from 1 and 3;

m is an integer selected among 0 and 1;

and furthermore $R_2$ is a $(C_1-C-7)$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

6. A compound according to claim 1 wherein R, $R_1$, $R_2$ and X have the meanings as defined in formula I, $R_3$ is a hydroxy group and $R_4$ is a hydrogen atom.

7. A compound according to claim 6 wherein $R_1$ is a hydrogen atom or methyl and X is a —C(=O)—, —C(=O)—N— or —$SO_2$— group.

8. A compound according to claim 7 wherein $R_2$ is a hydrogen atom, a $(C_1-C_4)$-alkoxy-$(C_1-C_3)$-alkyl group, a $(C_5-C_7)$-cycloalkyl group, a phenyl or a five- or six-membered heteroaryl having from one to three heteroatoms selected among nitrogen, oxygen and sulphur, a phenyl-$(C_1-C_4)$alkyl or heteroaryl-$(C_1-C_4)$-alkyl group optionally substituted by a substituent selected among a $(C_1-C_4)$-alkyl group, a $(C_1-C_4)$-alkoxy group and halogen, or a chain of formula

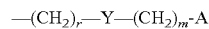

wherein

A is a phenyl or a heteroaryl selected among furan, thiophene, oxazole, imidazole, pyridine, pyrimidine and triazole both ones optionally substituted by a substituent selected among a $(C_1-C_4)$-alkyl group, a $(C_1-C_4)$-alkoxy group or halogen;

Y represents O, S or $NR_6$ wherein $R_6$ is a hydrogen atom or methyl;

r is an integer comprised between 1 and 3;

m is an integer selected among 0 and 3;

and furthermore $R_2$ is a $(C_1-C_7)$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

9. A compound according to claim 8 wherein $R_1$ is methyl and $R_2$ is a hydrogen atom, a methoxy-$(C_1-C_3)$-alkyl group, a $(C_5-C_7)$-cycloalkyl group, a phenyl or a heteroaryl selected among furan, thiophene, oxazole and pyridine, a benzyl or heteroaryl-methyl group wherein heteroaryl is selected among furan, thiophene, oxazole and pyridine, optionally substituted by a substituent selected among a $(C_1-C_4)$-alkyl group, a metoxy group and halogen, or a chain of formula

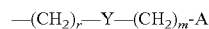

wherein

A is a phenyl or a heteroaryl selected among furan, thiophene, oxazole and pyridine, both ones optionally substituted by a substituent selected among a methyl group, a metoxy group or halogen;

Y represents O, S or $NR_6$ wherein $R_6$ is a hydrogen atom;

r is an integer comprised between 1 and 3;

m is an integer selected among 0 and 1;

and furthermore $R_2$ is a $(C_1-C_7)$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

10. A compound according to claim 9 wherein $R_2$ is a methoxy-methyl group, a cycloesyl, a phenyl or a heteroaryl selected among furan, thiophene, oxazole and pyridine, a benzyl or thiophen-il-methyl group optionally substituted by a substituent selected among a methyl group, a metoxy group and halogen, or a chain of formula

—(CH$_2$)$_r$—Y—(CH$_2$)$_m$-A wherein

A is a phenyl or pyridine, both ones optionally substituted by a metoxy group;

Y represents O, S or $NR_6$ wherein $R_6$ is a hydrogen atom;

r is an integer comprised between 1 and 3;

m is an integer selected between 0 and 1;

and furthermore $R_2$ is a $(C_1-C_7)$-alkyl group or a $(C_4-C_{10})$-alkyl group when, at the same time, X is a —C(=O)— group, $R_1$ is a $(C_1-C_3)$-alkyl group and $R_3$ is a hydroxy group or $R_3$ taken together with $R_4$ forms a =N—O—$R_5$ group wherein $R_5$ is different from —X—$R_2$.

11. A compound according to claim 1 wherein the —X—$R_2$ substituent in the meanings of $R_5$ has the same meanings of the X and $R_2$ substituents at 3' position.

12. A process for the preparation of a compound according to claim 1 which comprises:

a. the demethylation of the dimethylamino group at 3' position of a compound of formula

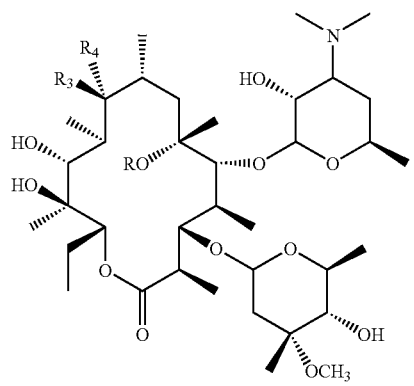

(II)

wherein

R, $R_3$ and $R_4$ are as defined as in claim 1;

b. the removal of L-cladinose by a hydrolysis reaction;

c. the amidation reaction of the primary or secondary aminic group obtained by item a.

13. A process according to claim 12 wherein $R_3$ in formula II is a hydroxy group and $R_4$ is a hydrogen atom.

14. A process according to claim 12 wherein the removal of the cladinose is carried out by an acid catalyzed hydrolysis in presence of a mineral acid and of a protic organic solvent.

15. A pharmaceutical composition comprising a therapeutically effective amount of a compound according to claim 1 in admixture with a pharmaceutically acceptable carrier.

16. A pharmaceutical composition according to claim 15 useful in the treatment of inflammatory diseases.

17. A pharmaceutical composition according to claim 15 useful in the treatment of respiratory diseases.

18. A pharmaceutical composition according to claim 16 useful in the treatment of gastrointestinal diseases.

* * * * *